(12) United States Patent
Yamazaki et al.

(10) Patent No.: US 10,538,564 B2
(45) Date of Patent: Jan. 21, 2020

(54) PEPTIDES HAVING OSTEOBLAST GROWTH-PROMOTING ACTIVITY AND USE THEREOF

(71) Applicant: PHARMA FOODS INTERNATIONAL CO., LTD., Kyoto (JP)

(72) Inventors: Chihiro Yamazaki, Kyoto (JP); Ji-Yeong An, Kyoto (JP); Seiyu Harada, Kyoto (JP); Kazuya Watabe, Kyoto (JP); Mujo Kim, Kyoto (JP)

(73) Assignee: PHARMA FOODS INTERNATIONAL CO., LTD., Kyoto (JP)

( * ) Notice: Subject to any disclaimer, the term of this patent is extended or adjusted under 35 U.S.C. 154(b) by 0 days.

(21) Appl. No.: 15/121,471

(22) PCT Filed: Feb. 25, 2015

(86) PCT No.: PCT/JP2015/055340
§ 371 (c)(1),
(2) Date: Aug. 25, 2016

(87) PCT Pub. No.: WO2015/129726
PCT Pub. Date: Sep. 3, 2015

(65) Prior Publication Data
US 2016/0362466 A1 Dec. 15, 2016

(30) Foreign Application Priority Data
Feb. 25, 2014 (JP) .................................. 2014-034240

(51) Int. Cl.
| | | |
|---|---|---|
| A61K 38/04 | (2006.01) | |
| A61K 38/08 | (2019.01) | |
| A61K 38/10 | (2006.01) | |
| C07K 7/04 | (2006.01) | |
| C07K 7/06 | (2006.01) | |
| C07K 7/08 | (2006.01) | |
| A23L 33/18 | (2016.01) | |
| C07K 14/51 | (2006.01) | |
| A61K 8/64 | (2006.01) | |
| A61K 38/00 | (2006.01) | |

(52) U.S. Cl.
CPC .............. *C07K 14/51* (2013.01); *A23L 33/18* (2016.08); *A61K 8/64* (2013.01); *A61K 38/04* (2013.01); *A61K 38/08* (2013.01); *A61K 38/10* (2013.01); *C07K 7/04* (2013.01); *C07K 7/06* (2013.01); *C07K 7/08* (2013.01); *A23V 2002/00* (2013.01); *A61K 38/00* (2013.01)

(58) Field of Classification Search
None
See application file for complete search history.

(56) References Cited

U.S. PATENT DOCUMENTS

| 5,366,871 A | 11/1994 | Rechsteiner et al. |
| 2015/0164973 A1 | 6/2015 | Kim et al. |

FOREIGN PATENT DOCUMENTS

| JP | 4-53471 | 2/1992 |
| JP | 2006-115761 | 5/2006 |
| JP | 2009-247459 | 10/2009 |
| JP | 2011-211979 | 10/2011 |
| WO | 2011/122127 | 10/2011 |
| WO | 2012/167370 | 12/2012 |
| WO | WO 2012/167370 | * 12/2012 |
| WO | 2014/007318 | 1/2014 |

OTHER PUBLICATIONS

Vogel et al., Curr. Opin. Struc. Biol., 2004, vol. 14(2):208-216.*
International Search Report dated Apr. 21, 2015 in International Application No. PCT/JP2015/055340.
Shun-ichiro, Iemura et al., "Isolation and Characterization of Bone Morphogenetic Protein-binding Proteins from the Early *Xenopus* Embryo*", The Journal of Biological Chemistry, vol. 274, No. 38, pp. 26843-26849; 1999.
Jess Liu et al., "Novel bioactivity of phosvitin in connective tissue and bone organogenesis revealed by live calvarial bone organ culture models", Developmental Biology, vol. 381, pp. 256-275, 2013.
T. Saito et al., "Mineral Induction by Immobilized Phosphoproteins", Bone, vol. 21, No. 4, pp. 305-311, 1997.
Shun-ichiro, Iemura et al., "Isolation and Characterization of Bone Morphogenetic Protein-binding Proteins from the Early *Xenopus* Embryo*", The Journal of Biological Chemistry, vol. 274, No. 38, pp. 26848-26849; 1999.
Jiandong Ren, University of Alberta, "Phosvitin extraction and phosphopeptides characterization from chicken egg yolk", Aug. 27, 2012.
Inwook Choi et al., "Effectiveness of phosvitin peptides on enhancing bioavailability of calcium and its accumulation in bones", Food Chemistry, Elsevier Ltd, NL, vol. 93, No. 4, Dec. 1, 2005.
International Preliminary Report on Patentability dated Aug. 30, 2016 in International Application No. PCT/JP2015/055340.

(Continued)

*Primary Examiner* — Xiaozhen Xie
(74) *Attorney, Agent, or Firm* — Wenderoth, Lind & Ponack, L.L.P.

(57) ABSTRACT

The present invention provides a novel peptide having bone formation-promoting effect and chondrocyte growth-promoting effect, in particular, a peptide having osteoblast growth-promoting activity, having 100 amino acid residues or less comprising an amino acid sequence selected from
(a) Val-Asn-Pro-Glu-Ser-Glu-Glu-Glu-Asp-Glu-Ser-Ser-Pro-Tyr-Glu (SEQ ID NO: 1),
(b) an amino acid sequence derived from the amino acid sequence (a) by conservative substitution or deletion of 1 to 3 amino acids, and
(c) an amino acid sequence consisting of at least four contiguous amino acids of the amino acid sequence (a) or (b), or
a derivative thereof or a salt thereof.

5 Claims, 16 Drawing Sheets

Specification includes a Sequence Listing.

(56) References Cited

OTHER PUBLICATIONS

Extended European Search Report dated Sep. 20, 2017 in corresponding European patent application No. 15755196.1.
Jiandong Ren, University of Alberta, "Phosvitin extraction and phosphopeptides characterization from chicken egg yolk", Aug. 27, 2012. (Thesis).
Inwook Choi et al., "Effectiveness of phosvitin peptides on enhancing bioavailability of calcium and its accumulation in bones", Food Chemistry, vol. 93, No. 4, Dec. 1, 2005, pp. 577-583.

* cited by examiner

Fig. 8

```
                          P
                          |
No.1:   Val-Asn-Pro-Glu-Ser-Glu-Glu-Glu  (SEQ ID NO: 9)

P
                          |
No.2:   Val-Asn-Pro-Glu-Ser-Glu-Glu  (SEQ ID NO: 10)

P
                  |
No.3:   Pro-Glu-Ser-Glu-Glu  (SEQ ID NO: 11)

P
                  |
No.4:   Asp-Glu-Ser-Ser-Pro-Tyr-Glu  (SEQ ID NO: 12)

P
                      |
No.5:   Glu-Asp-Glu-Ser-Ser-Pro-Tyr-Glu  (SEQ ID NO: 13)

P                           P
                          |                           |
No.6:   Val-Asn-Pro-Glu-Ser-Glu-Glu-Glu-Asp-Glu-Ser-Ser-Pro-Tyr-Glu (SEQ ID NO: 14)
```

PF-201 : 100 mg/kg/day (p.o)
hGH : 500 μg/kg/day (s.c)

TC: tetracycline (fluorescent label), CL: calcein (fluorescent label)

*$P<0.05$, **$P<0.01$ scale bar : 500 μm

TC: tetracycline (fluorescent label), CL: calcein (fluorescent label)

*P<0.05, **P<0.01

*P<0.05

TC: tetracycline (fluorescent label), CL: calcein (fluorescent label)

a:P<0.05, b:P<0.01, c:P<0.001 compared with the control group,
d:P<0.05, e:P<0.01, f:P<0.001 compared with the hGH group.

a:$P<0.05$, b:$P<0.01$, c:$P<0.001$ compared with the control group,
d:$P<0.05$, e:$P<0.01$, f:$P<0.001$ compared with the hGH group.

a: $P<0.05$ compared with the control group.

PEPTIDES HAVING OSTEOBLAST GROWTH-PROMOTING ACTIVITY AND USE THEREOF

TECHNICAL FIELD

The present invention relates to a peptide having osteoblast growth-promoting activity; a bone formation promoter, a bone resorption inhibitor, a chondrocyte growth promoter, a hyaluronic acid production promoter, a chondrogenic cell differentiation inducer, a mesenchymal stem cell growth promoter and a mesenchymal stem cell differentiation inducer, each comprising the peptide; and use thereof.

BACKGROUND ART

Osteoporosis is a systemic disease that develops due to reduction of the bone volume or the bone mineral content and causes the breakage of the fine structure of bone, which reduces the bone strength and increases the risk of bone fracture. The number of patients with osteoporosis in Japan reaches about 11 million, and 80% of them are women. Osteoporosis mainly affects people in their middle or older age, and considering that the society is aging, the number of patients is expected to increase in the future. Another concern is that the incidence of bone fracture is increasing in elementary and junior high school students. In order to prevent osteoporosis, it is very important to substantially increase the bone mineral content during the young age, thus achieving a high peak bone mass. Thus the maintenance of bone health is now a social interest regardless of sex and age.

Bone diseases are conventionally prevented or treated by dietary calcium supplementation, light exercise, sun bath, medication, etc. Such dietary calcium supplementation is done with calcium salts such as calcium carbonate and calcium phosphate, and natural calcium sources such as bovine bone powder, egg shells and fish bone powder. However, such ingredients are not very suitable for oral ingestion in terms of solubility, absorptivity and taste. Moderate exercise increases the bone volume and strengthens bone, and a stroll and a walk are good for bone health. However, for people with low physical strength, even light exercise is troublesome, and exercise is almost impossible for the bedridden elderly. Sun bath is considered to be good for supply of activated vitamin $D_3$, but sun bath is insufficient for prevention or treatment of bone diseases.

For the prevention or treatment of various chondropathies, the growth of chondrocytes and the expression of differentiation function are important. That is, the growth and maturation of chondrocytes are considered to promote normal growth of bone and repair bone fracture. Several factors for inducing the growth of chondrocytes have been reported, including transforming growth factor (TGF)-$\beta$1, insulin-like growth factor (IGF)-1, basic fibroblast growth factor (bFGF), PTH-related peptide (PTHrP), hepatocyte growth factor (HGF), and bone morphogenetic protein (BMP). However, clinical applications of chondrocyte growth-promoting drugs excellent in safety, stability and efficacy have not been established yet.

Patients with osteoarthritis account for the largest proportion of chondropathy patients. One of the causes of osteoarthritis may be aging, and the incidence of the disease is expected to increase in this aging society. Conventionally, bone resorption inhibitors such as estrogen and calcitonin, aspirin, and nonsteroidal anti-inflammatory drugs (NSAIDs) have mostly been used for the prevention and treatment of cartilage disorders that manifest degeneration of cartilage as major symptoms, such as joint diseases. However, these drugs are not effective enough, and are well-known to cause adverse reactions such as digestive tract disorders. Under these circumstances, there has been a great demand for prophylactic or alleviating drugs that are safe for use in the treatment of cartilage injuries and cartilage disorders.

The inventors found that an egg yolk-derived peptide comprising an amino acid sequence comprising at least Ala-Glu-Ser has osteoblast growth-promoting activity (see Patent Literature 1) and that an egg-yolk protein hydrolysate has chondrocyte growth-promoting activity (see Patent Literature 2). The inventors then filed a patent based on these findings.

CITATION LIST

Patent Literature

Patent Literature 1: JP 2011-211979 A
Patent Literature 2: WO 2014/007318

SUMMARY OF INVENTION

Technical Problem

An object of the present invention is to provide a novel peptide having bone formation-promoting effect and chondrocyte growth-promoting effect and to provide excellent applications of the peptide.

Solution to Problem

The present invention has been made to solve the above problems and includes the following.
[1] A peptide having osteoblast growth-promoting activity, having 100 amino acid residues or less comprising an amino acid sequence selected from
(a)    Val-Asn-Pro-Glu-Ser-Glu-Glu-Glu-Asp-Glu-Ser-Ser-Pro-Tyr-Glu (SEQ ID NO: 1),
(b) an amino acid sequence derived from the amino acid sequence (a) by conservative substitution or deletion of 1 to 3 amino acids, and
(c) an amino acid sequence consisting of at least four contiguous amino acids of the amino acid sequence (a) or (b), or
a derivative thereof or a salt thereof.
[2] The peptide of the above [1] or a derivative thereof or a salt thereof, which has at least one phosphorylated serine.
[3] The peptide of the above [1] or [2] or a derivative thereof or a salt thereof, which is a fragment of lipovitellin-1.
[4] The peptide of any one of the above [1] to [3] or a derivative thereof or a salt thereof, which further has chondrocyte growth-promoting activity and/or hyaluronic acid production-promoting activity.
[5] The peptide of any one of claims 1 to 4 or a derivative thereof or a salt thereof, which consists of an amino acid sequence selected from

```
                                         (SEQ ID NO: 1)
  (i) Val-Asn-Pro-Glu-Ser-Glu-Glu-Glu-Asp-Glu-Ser-
      Ser-Pro-Tyr-Glu,
                                         (SEQ ID NO: 2)
 (ii) Val-Asn-Pro-Glu-Ser-Glu-Glu-Glu,
                                         (SEQ ID NO: 3)
(iii) Val-Asn-Pro-Glu-Ser-Glu-Glu,
```

-continued (iv) Pro-Glu-Ser-Glu-Glu, (SEQ ID NO: 4)

(v) Asp-Glu-Ser-Ser-Pro-Tyr-Glu, (SEQ ID NO: 5)
and (vi) Glu-Asp-Glu-Ser-Ser-Pro-Tyr-Glu. (SEQ ID NO: 6)

[6] A polynucleotide encoding the peptide of any one of the above [1] to [5].

[7] An expression vector comprising the polynucleotide of the above [6].

[8] A transformant resulting from transformation with the recombinant vector of the above [7].

[9] A bone formation promoter comprising the peptide of any one of the above [1] to [5] or a derivative thereof or a salt thereof or lipovitellin-1 or a derivative thereof or a salt thereof.

[10] The bone formation promoter of the above [9], which has osteoblast growth-promoting effect.

[11] A bone resorption inhibitor comprising the peptide of any one of the above [1] to [5] or a derivative thereof or a salt thereof or lipovitellin-1 or a derivative thereof or a salt thereof.

[12] A chondrocyte growth promoter comprising the peptide of any one of the above [1] to [5] or a derivative thereof or a salt thereof or lipovitellin-1 or a derivative thereof or a salt thereof.

[13] A hyaluronic acid production promoter comprising the peptide of any one of the above [1] to [5] or a derivative thereof or a salt thereof or lipovitellin-1 or a derivative thereof or a salt thereof.

[14] A chondrogenic cell differentiation inducer comprising the peptide of any one of the above [1] to [5] or a derivative thereof or a salt thereof or lipovitellin-1 or a derivative thereof or a salt thereof.

[15] A mesenchymal stem cell growth promoter comprising the peptide of any one of the above [1] to [5] or a derivative thereof or a salt thereof or lipovitellin-1 or a derivative thereof or a salt thereof.

[16] A mesenchymal stem cell differentiation inducer comprising the peptide of any one of the above [1] to [5] or a derivative thereof or a salt thereof or lipovitellin-1 or a derivative thereof or a salt thereof.

[17] The promoter, inhibitor or inducer of any one of the above [9] to [16], which is for oral administration.

[18] A medicament comprising the peptide of any one of the above [1] to [5] or a derivative thereof or a salt thereof or lipovitellin-1 or a derivative thereof or a salt thereof.

[19] The medicament of the above [18], for promoting bone formation or for preventing or alleviating a cartilage disorder or a joint disease.

[20] A food or drink product comprising the peptide of any one of the above [1] to [5] or a derivative thereof or a salt thereof or lipovitellin-1 or a derivative thereof or a salt thereof.

[21] The food or drink product of the above [20], for promoting bone formation or for preventing or alleviating a cartilage disorder or a joint disease.

[22] A supplement comprising the peptide of any one of the above [1] to [5] or a derivative thereof or a salt thereof or lipovitellin-1 or a derivative thereof or a salt thereof.

[23] The supplement of the above [22], for promoting bone formation or for preventing or alleviating a cartilage disorder or a joint disease.

[24] A food additive comprising the peptide of any one of the above [1] to [5] or a derivative thereof or a salt thereof or lipovitellin-1 or a derivative thereof or a salt thereof.

[25] The food additive of the above [24], for promoting bone formation or for preventing or alleviating a cartilage disorder or a joint disease.

[26] A cosmetic product comprising the peptide of any one of the above [1] to [5] or a derivative thereof or a salt thereof or lipovitellin-1 or a derivative thereof or a salt thereof.

[27] The cosmetic product of the above [26], for promoting bone formation or for preventing or alleviating a cartilage disorder or a joint disease.

[28] A method for promoting bone formation, the method comprising administering, to a mammal, an effective amount of the peptide of any one of the above [1] to [5] or a derivative thereof or a salt thereof or lipovitellin-1 or a derivative thereof or a salt thereof.

[29] A method for preventing or alleviating a cartilage disorder or a joint disease, the method comprising administering, to a mammal, an effective amount of the peptide of any one of the above [1] to [5] or a derivative thereof or a salt thereof or lipovitellin-1 or a derivative thereof or a salt thereof.

[30] The peptide of any one of the above [1] to [5] or a derivative thereof or a salt thereof or lipovitellin-1 or a derivative thereof or a salt thereof for use in the promotion of bone formation or the prevention or alleviation of a cartilage disorder or a joint disease.

[31] Use of the peptide of any one of the above [1] to [5] or a derivative thereof or a salt thereof or lipovitellin-1 or a derivative thereof or a salt thereof for the promotion of bone formation or for the prevention or alleviation of a cartilage disorder or a joint disease.

[32] Use of the peptide of any one of the above [1] to [5] or a derivative thereof or a salt thereof or lipovitellin-9 or a derivative thereof or a salt thereof for the production of a medicament for promoting bone formation or for preventing or alleviating a cartilage disorder or a joint disease.

Advantageous Effects of Invention

The present invention provides a novel peptide having bone formation-promoting effect and chondrocyte growth-promoting effect. The peptide can promote bone formation via oral ingestion, and is thus useful as a medicament, a food or drink product, a supplement, a food additive, a cosmetic product, etc. that are for promoting bone formation or for preventing or alleviating a cartilage disorder or joint pain.

BRIEF DESCRIPTION OF DRAWINGS

FIG. 8 shows the analysis results of the structure of peptides.

DESCRIPTION OF EMBODIMENTS

Peptides

Figure 1:
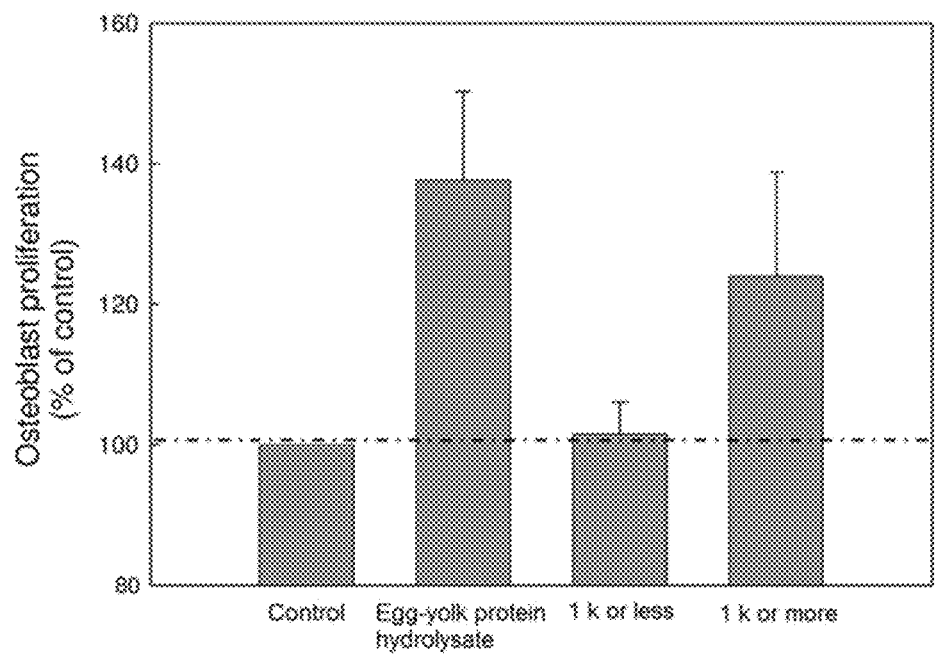
FIG. 1 shows a chart showing the measurement results of the osteoblast growth-promoting activity of fractions resulting from fractionation of an egg-yolk protein hydrolysate with a UF membrane with a cut-off molecular weight of 1 kDa.

The present invention provides a peptide having osteoblast growth-promoting activity.

The inventors investigated the identification of peptides with strong activity for promoting the growth of osteoblasts from a peptide mixture obtained by hydrolysis of egg yolk proteins, and isolated the peptides consisting of the amino acid sequences (i) to (vi) shown below. The amino acid sequences (ii) to (vi) are partial sequences of the amino acid sequence (i).

```
                                            (SEQ ID NO: 1)
(i)   Val-Asn-Pro-Glu-Ser-Glu-Glu-Glu-Asp-Glu-Ser-
      Ser-Pro-Tyr-Glu (SEQ ID NO: 2)
(ii)  Val-Asn-Pro-Glu-Ser-Glu-Glu-Glu (SEQ ID NO: 3)
(iii) Val-Asn-Pro-Glu-Ser-Glu (SEQ ID NO: 4)
(iv)  Pro-Glu-Ser-Glu-Glu (SEQ ID NO: 5)
(v)   Asp-Glu-Ser-Ser-Pro-Tyr-Glu (SEQ ID NO: 6)
(vi)  Glu-Asp-Glu-Ser-Ser-Pro-Tyr-Glu
```

The peptide provided by the present invention is a peptide having osteoblast growth-promoting activity, comprising an amino acid sequence selected from
(a) Val-Asn-Pro-Glu-Ser-Glu-Glu-Glu-Asp-Glu-Ser-Ser-Pro-Tyr-Glu (SEQ ID NO: 1),
(b) an amino acid sequence derived from the amino acid sequence (a) by conservative substitution or deletion of 1 to 3 amino acids, and
(c) an amino acid sequence consisting of at least four contiguous amino acids of the amino acid sequence (a) or (b).

The peptide of the present invention may be a peptide consisting of the amino acid sequence (a), (b) or (c), or a peptide comprising the amino acid sequence (a), (b) or (c) and an amino acid sequence other than (a), (b) or (c). In cases where the peptide of the present invention comprises an amino acid sequence other than (a), (b) or (c), the amino acid sequence other than (a), (b) or (c) is not particularly limited as long as the peptide retains osteoblast growth-promoting activity. The amino acid sequence other than (a), (b) or (c) may be, for example, a tag sequence (e.g., a polyhistidine tag, a Myc tag, a FLAG tag, etc.).

The number of the amino acid residues contained in the peptide of the present invention is not particularly limited, but is preferably 1000 or less, more preferably 500 or less, further more preferably 200 or less, further more preferably 100 or less, further more preferably 80 or less, further more preferably 70 or less, further more preferably 60 or less, further more preferably 50 or less, further more preferably 40 or less, further more preferably 30 or less, further more preferably 20 or less, particularly preferably 15 or less. The minimum number of the amino acid residues is not particularly limited as long as the peptide retains osteoblast growth-promoting activity, but the minimum number of the amino acid residues is preferably 3 or more, more preferably 4 or more, further more preferably 5 or more.

A homology search revealed that the amino acid sequence of SEQ ID NO: 1 corresponds to positions 1060 to 1074 of the amino acid sequence of vitellogenin-2 (SEQ ID NO: 7), which is a precursor protein contained in an egg yolk. The peptide of the present invention is, hence, preferably a fragment of vitellogenin-2 that contains at least four contiguous amino acids at positions 1060 to 1074 of vitellogenin-2 and has osteoblast growth-promoting activity.

Vitellogenin-2 is a precursor protein contained in an egg yolk, and is known to be cleaved into four yolk proteins: lipovitellin-1, phosvitin, lipovitellin-2 and YGP40 (yolk glycoprotein of 40 kDa) (see the database UniProt: P02845 (VIT2_CHICK)). Positions 1060 to 1074 of vitellogenin-2 corresponds to positions 1045 to 1059 of the amino acid sequence of lipovitellin-1 (SEQ ID NO: 8). The peptide of the present invention is, hence, preferably a fragment of lipovitellin-2 that contains at least four contiguous amino acids at positions 1045 to 1059 of lipovitellin-1 and has osteoblast growth-promoting activity.

Preferably, the peptide of the present invention is a peptide consisting of any of the amino acid sequences (i) to (vi).

The term "conservative substitution of amino acids" herein means substitution of an amino acid for another one within the same group shown in Table 1 below. In Table 1, preferred conservative substitutions of amino acids include a substitution between aspartic acid and glutamic acid, a substitution among arginine, lysine, and histidine, a substitution between tryptophan and phenylalanine, a substitution between phenylalanine and valine, a substitution among leucine, isoleucine and alanine, and a substitution between glycine and alanine.

TABLE 1

| | |
|---|---|
| Acidic amino acids | Aspartic acid (D), glutamic acid (E) |
| Basic amino acids | Arginine (R), lysine (K), histidine (H) |
| Hydrophilic amino acids | Serine (S), threonine (T), asparagine (N), glutamine (Q) |
| Hydrophobic amino acids | Tryptophan (W), phenylalanine (F), valine (V), leucine (L), isoleucine (I), methionine (M), proline (P), alanine (A) |
| Aromatic amino acids | Tyrosine (Y), tryptophan (W), phenylalanine (F) |
| Hydroxyamino acids | Serine (S), threonine (T) |
| Sulfur-containing amino acids | Cysteine (C), cystine, methionine (M) |
| Small amino acids | Glycine (G), alanine (A), serine (S), methionine (M), threonine (T) |

The peptide derivative of the present invention is derived from a peptide with a particular amino acid sequence and the C-terminus of the peptide derivative may be a carboxyl group (—COOH), a carboxylate (—COO⁻), an amide (—CONH$_2$) or an ester (—COOR). Examples of R of the ester include $C_{1-6}$ alkyl groups such as methyl, ethyl, n-propyl, isopropyl and n-butyl; $C_{3-8}$ cycloalkyl groups such as cyclopentyl and cyclohexyl; $C_{6-12}$ aryl groups such as phenyl and α-naphthyl; $C_{7-14}$ aralkyl groups including phenyl-$C_{1-2}$ alkyl groups, such as benzyl and phenethyl, and α-naphthyl-$C_{1-2}$ alkyl groups, such as α-naphthylmethyl; and a pivaloyloxymethyl group, which is commonly used as an ester for oral administration. Examples of the amide include an amide; an amide substituted with one or two $C_{1-6}$ alkyl groups; an amide substituted with one or two $C_{1-6}$ alkyl groups substituted with a phenyl group; and an amide that forms a 5- to 7-membered azacycloakane containing the nitrogen atom of the amide group. When the peptide of the present invention has a carboxyl group or a carboxylate at a position other than the C-terminus, those with amidated or esterified carboxyl or carboxylate are also included in the peptide derivative of the present invention.

The peptide derivative of the present invention also includes the peptides of the present invention in which the N-terminal amino group is protected with a protecting group (e.g., a $C_{1-6}$ acyl group including a formyl group and $C_{2-6}$ alkanoyl groups such as acetyl), the peptides of the present invention in which a N-terminal glutamyl group generated by in vivo cleavage of the N-terminus is converted to a pyroglutamate, and the peptides of the present invention in which a substituent (e.g., —OH, —SH, an amino group, an imidazole group, an indole group, or a guanidino group) on an amino acid side chain in the molecule is protected with a suitable protecting group (e.g., a $C_{1-6}$ acyl group including a formyl group and $C_{2-6}$ alkanoyl groups such as acetyl).

The side chains of the amino acids constituting the peptide derivative of the present invention may be modified with a substituent. Examples of the substituent include, but are not limited to, a fluorine atom, a chlorine atom, a cyano group, a hydroxy group, a nitro group, an alkyl group, a cycloalkyl group, an alkoxy group, an amino group, and a phosphate group. The side-chain substituent may be protected with a protecting group. The derivative of the peptide of the present invention also includes glycopeptides, which are peptides having sugar chains.

The peptide of the present invention or a derivative thereof may form a salt. The salt is preferably physiologically acceptable. Examples of the physiologically acceptable salt include salts with acids such as hydrochloric acid, sulfuric acid, phosphoric acid, lactic acid, tartaric acid, maleic acid, fumaric acid, oxalic acid, malic acid, citric acid, oleic acid, and palmitic acid; salts with hydroxides or carbonates of an alkali metal, such as sodium, potassium and calcium, salts with hydroxides or carbonates of an alkaline earth metal, and salts with aluminum hydroxide or carbonate; and salts with triethylamine, benzylamine, diethanolamine, t-butylamine, dicyclohexylamine, arginine, etc.

The peptide of the present invention or a derivative thereof may comprise a D-amino acid or a non-naturally occurring amino acid to the extent that the peptide or derivative retains its characteristics. The peptide of the present invention or a derivative thereof may comprise another substance linked thereto to the extent that the peptide or derivative retains its characteristics. Examples of the substance linkable to the peptide include other peptides, lipids, sugars, sugar chains, an acetyl group, and naturally occurring or synthetic polymers. The peptide of the present invention may be subjected to modification such as glycosylation, side-chain oxidation, and phosphorylation to the extent that the resulting modified peptide retains the characteristics of the original peptide.

The peptide of the present invention or a derivative thereof or a salt thereof preferably has at least one phosphorylated serine. The position of the phosphorylated serine is not particularly limited, but preferably at least one of the serine residues at positions 5, 11 and 12 of the amino acid sequence of SEQ ID NO: 1 is phosphorylated, more preferably at least one of the serine residues at positions 5 and 11 is phosphorylated, and further more preferably the serine residues at positions 5 and 11 are phosphorylated. Phosphorylation of the serine residue(s) has been shown to result in an increase in the effect of promoting the growth of bone-forming cells.

Figure 10:
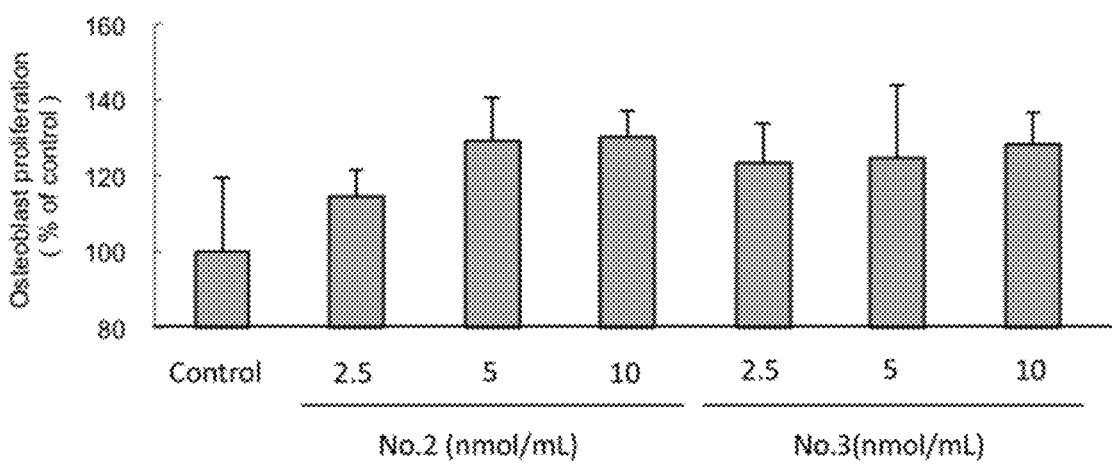
FIG. 10 is a chart showing the measurement results of the osteoblast growth-promoting activity of synthetic peptides (No. 2 and No. 3).

Preferred peptide derivatives of the present invention are peptides with a phosphorylated serine residue represented by the amino acid sequences of SEQ ID NOs: 9 to 14 (see FIG. 10).

The peptide of the present invention or a derivative thereof or a salt thereof (hereinafter the peptide, the derivative and the salt are collectively and simply called "the peptide of the present invention") can be produced by solid-phase synthesis (the Fmoc or Boc method) or liquid-phase synthesis in accordance with a known standard peptide synthesis protocol. Alternatively, the peptide of the present invention can be produced by using a transformant carrying an expression vector containing a DNA encoding the peptide of the present invention. Alternatively, the peptide of the present invention can be produced by preparing a peptide using a transformant carrying an expression vector containing a DNA encoding a peptide comprising the peptide of the present invention, and cleaving the resulting peptide with a suitable protease or peptidase. Alternatively, the peptide of the present invention can be produced by a method using an in vitro transcription-translation system.

The peptide of the present invention can be obtained by purifying a hydrolysate of chicken egg yolk proteins. The preparation method of a hydrolysate of egg yolk proteins and the purification method of the peptide are not particularly limited, and the preparation and purification may be done by a known method selected as appropriate. Specifically, the peptide can be obtained by, for example, preparing a defatted egg yolk powder, then preparing a hydrolysate from the powder using an enzyme such as a protease, and purifying a peptide of interest from the hydrolysate by ultrafiltration or chromatography such as HPLC.

Whether the peptide of interest has osteoblast growth-promoting activity can be determined by comparing the growth of osteoblasts between the culture in the presence of the peptide and the culture in the absence of the peptide in a test system selected as appropriate from known methods for measuring the cell growth. A higher growth level of osteoblasts in the culture in the presence of the peptide indicates that the peptide has the promoting activity. Specifically, for example, MTT assay or cell counting method may be performed in a cell culture system using an osteoblast-derived cell line.

Whether the peptide of interest has chondrocyte growth-promoting activity can be determined by comparing the growth of chondrocytes or chondrogenic cells between the culture in the presence of the peptide and the culture in the absence of the peptide in a test system selected as appropriate from known methods for measuring the cell growth. A higher growth level of osteoblasts in the culture in the presence of the peptide indicates that the peptide has the promoting activity. Specifically, for example, MTT assay or cell counting method may be performed in a cell culture system using an osteoblast-derived cell line.

Whether the peptide of interest has hyaluronic acid production-promoting activity can be determined by measuring, by a known method, the amounts of hyaluronic acid production in the culture supernatant in culture using cultured cells with an ability to produce hyaluronic acid, and then comparing the amounts of hyaluronic acid between the culture in the presence of the peptide and the culture in the absence of the peptide. A higher amount of hyaluronic acid in the supernatant of the culture in the presence of the peptide indicates that the peptide has the promoting activity. Examples of the measurement method of the amount of hyaluronic acid include ELISA.

Polynucleotides

The polynucleotide provided by the present invention is a polynucleotide encoding the above peptide of the present invention. The polynucleotide can be present in the form of RNA (e.g., mRNA) or DNA (e.g., cDNA or genomic DNA). The polynucleotide may be a double or single strand. The double strand may be a double-stranded DNA, a double-stranded RNA or a DNA-RNA hybrid. The single strand may be a coding strand (sense strand) or a non-coding strand (antisense strand). The polynucleotide of the present invention may be fused with a polynucleotide encoding a tag label (a tag sequence or a marker sequence) at the 5'- or 3'-terminus. The polynucleotide of the present invention may contain an untranslated region (UTR) sequence, a vector sequence (including an expression vector sequence), etc.

The nucleotide sequence of the polynucleotide encoding the peptide of the present invention can be custom designed by appropriately selecting codons for amino acids based on the amino acid sequence of the peptide of the present invention and combining the selected codons. As described above, the amino acid sequence of SEQ ID NO: 1 is part of the amino acid sequence of vitellogenin-2 (SEQ ID NO: 7), which is a precursor protein contained in an egg yolk, and therefore the nucleotide sequence of the polynucleotide can be designed based on the nucleotide sequence of the gene encoding vitellogenin-2.

The polynucleotide of the present invention can be produced by a known DNA synthesis method, PCR, etc. Specifically, for example, the nucleotide sequence is designed by appropriately selecting codons for amino acids based on the amino acid sequence of the peptide of the present invention, and the designed sequence is chemically synthesized using a commercially available DNA synthesizer. Alternatively, primers are designed for amplification of the coding region of the peptide of the present invention in the nucleotide sequence of the gene encoding vitellogenin-2 (accession No.: X13607), and then PCR etc. are performed with chicken genomic DNA or cDNA as a template using the designed primers to produce a DNA fragment containing the polynucleotide of the present invention in large quantities.

Expression Vectors

The present invention provides an expression vector used for the production of the peptide of the present invention. The expression vector of the present invention is not particularly limited as long as it contains a polynucleotide encoding the peptide of the present invention, but preferred are plasmid vectors carrying a RNA polymerase recognition sequence (pSP64, pBluescript, etc.). The method for preparing the expression vector is not particularly limited, and the expression vector may be prepared with the use of a plasmid, a phage, a cosmid or the like. The type of the vector is not particularly limited and any appropriate vector that can be expressed in host cells can be selected. For example, a promoter sequence is selected as appropriate for the type of host cells to ensure the expression of the polynucleotide of the present invention, and this promoter sequence and the polynucleotide of the present invention are inserted into a plasmid etc. to give a desired expression vector. After a host transformed with the expression vector of the present invention is cultured, cultivated or bred, the peptide of the present invention can be collected and purified from the culture products etc. by conventional methods (e.g., filtration, centrifugation, cell disruption, gel filtration chromatography, ion exchange chromatography, etc.).

The expression vector preferably contains at least one selection marker. Examples of the marker include a dihydrofolate reductase gene and a neomycin resistance gene for eukaryote cell culture; and a tetracycline resistance gene and an ampicillin resistance gene for culture of *Escherichia coli* and other bacteria. Such a selection marker is useful for checking whether the polynucleotide of the present invention has been successfully transfected into host cells and whether the polynucleotide is reliably expressed therein. Alternatively, the peptide of the present invention may be expressed as a fusion protein. The peptide of the present invention may be expressed as, for example, a GFP fusion protein using green fluorescent protein (GFP) of *Aequorea victoria* as a marker.

The host is not particularly limited and various known cells can suitably be used. Specific examples of the cells include bacteria such as *Escherichia coli*, yeasts (budding yeast *Saccharomyces cerevisiae* and fission yeast *Schizosaccharomyces pombe*), nematodes (*Caenorhabditis elegans*), *Xenopus laevis* oocytes and animal cells (e.g., CHO cells, COS cells and Bowes melanoma cells). The method for transfecting host cells with the expression vector, i.e. the transformation method, is also not particularly limited and known nethods can suitably be used, including electroporation, the calcium phosphate method, the liposome method and the DEAE dextran method.

Transformants

The present invention provides a transformant carrying the expression vector of the present invention. As used herein, the transformant encompasses a cell, a tissue and an organ as well as an individual organism. The type of the organism to be transformed is not particularly limited, and examples thereof include various microorganisms, plants and animals listed above as examples of the host cells. The transformant of the present invention expresses the peptide of the present invention. It is preferred that the transformant of the present invention stably expresses the peptide of the present invention, but the transformant may transiently express the peptide.

Bone Formation Promoter, Bone Resorption Inhibitor, Chondrocyte Growth Promoter, Hyaluronic Acid Production Promoter, Chondrogenic Cell Differentiation Inducer, Mesenchymal Stem Cell Growth Promoter, and Mesenchymal Stem Cell Differentiation Inducer The present invention provides a bone formation promoter comprising the peptide of the present invention. Since the peptide of the present invention has bone formation-promoting activity, the peptide is suitable as an active ingredient for a bone formation promoter. The bone formation-promoting activity of the peptide of the present invention can be confirmed by, for example, administering (e.g., oral administering) the peptide of the present invention to an animal subject for a certain period of time (e.g., for 7, 14 or 21 days), and measuring an indicator for the activity, including an enhanced increase in the height of the tibial growth plate, an increase in the growth rate of the growth cartilage, promotion of the formation of the primary cancellous bone, an increase in the serum level of insulin-like growth factor (IGF-1), an increase in the secondary cancellous bone volume relative to the bone tissue volume, an increase of osteoblasts, a reduction of osteoclasts, an increase in the mineral apposition rate in the secondary cancellous bone, etc. The term "growth cartilage" herein refers to, for example, the growing area of the bone at the epiphysis. The term "primary cancellous bone" refers to, for example, immature cancellous bone immediately below the growth cartilage. The term "secondary cancellous bone" refers to, for example, mature cancellous bone. The term "promotion of bone formation" herein can be understood as "an enhanced increase in the height of the tibial growth plate", "an increase in the growth rate of the growth cartilage", "promotion of the formation of the primary cancellous bone", "an increase in the serum level of insulin-like growth factor (IGF-1)", "an increase in the secondary cancellous bone volume relative to the bone tissue volume", "an increase of osteoblasts", "a reduction of osteoclasts", "an increase in the mineral apposition rate in the secondary cancellous bone", etc. The present invention also provides an osteoblast growth promotor comprising the peptide of the present invention. Since the peptide of the present invention has osteoblast growth-promoting activity, the peptide is suitable as an active ingredient for an osteoblast growth promotor. The present invention also provides a bone resorption inhibitor comprising the peptide of the present invention. The peptide of the present invention has bone resorption-inhibiting activity, and is thus suitable as an active ingredient for a bone resorption inhibitor. The present invention also provides a chondrocyte growth promotor comprising the peptide of the present invention. Since the peptide of the present invention has chondrocyte growth-promoting activity, the peptide is suitable as an active ingredient for a chondrocyte growth promoter. The present invention also provides a hyaluronic acid production promoter comprising the peptide of the present invention. Since the peptide of the present invention has hyaluronic acid production-promoting activity, the peptide is suitable as an active ingredient for a hyaluronic acid production promoter. The present invention also provides a chondrogenic cell differentiation inducer comprising the peptide of the present invention. Since the peptide of the present invention has differentiation inducing activity on chondrogenic cells, the peptide is suitable as an active ingredient for a chondrogenic cell differentiation inducer. The present invention also provides a mesenchymal stem cell growth promoter comprising the peptide of the present invention. The peptide of the present invention has growth-promoting activity on mesenchymal stem cells, and is thus suitable as an active ingredient for a mesenchymal stem cell growth promoter. The present invention also provides a mesenchymal stem cell differentiation inducer comprising the peptide of the present invention. The peptide of the present invention has differentiation inducing activity on mesenchymal stem cells, and is thus suitable as an active ingredient for a mesenchymal stem cell differentiation inducer.

In addition to the peptide of the present invention, lipovitellin-1 or a derivative thereof or a salt thereof is also suitable as an active ingredient for the above promoter, inhibitor or inducer. The lipovitellin-1 herein refers to a protein that consists of an amino acid sequence identical or substantially identical to the amino acid sequence of SEQ ID NO: 8 and has substantially the same activity as that of lipovitellin-1. The amino acid sequence substantially identical to the amino acid sequence of SEQ ID NO: 8 is, for example, an amino acid sequence derived from SEQ ID NO: 8 by deletion, substitution or addition of one to several amino acids. The phrase "deletion, substitution or addition of one to several amino acids" means deletion, substitution or addition of amino acids whose number is substantially equal to the number of the residues that can be deleted, substituted or added by a known method for mutagenesis of peptides, such as site-directed mutagenesis (preferably 10 amino acids or less, more preferably 7 amino acids or less, and even more preferably 5 amino acids or less). Such a mutant protein is not limited to a protein artificially mutated by a known method for mutagenesis of polypeptides, and may be a protein isolated and purified from nature. In addition, the amino acid sequence substantially identical to the amino acid sequence of SEQ ID NO: 1 is, for example, an amino acid sequence that is at least 80% identical, more preferably at least 85%, 90%, 92%, 95%, 96%, 97%, 98% or 99% identical to the amino acid sequence of SEQ ID NO: 1.

A derivative of lipovitellin-1 is preferably those listed above as the examples of the derivative of the peptide of the present invention. A salt of lipovitellin-1 or of a derivative of lipovitellin-1 is preferably those listed above as the examples of the salt of the peptide of the present invention or of the derivative of the peptide of the present invention.

Lipovitellin-1, a derivative thereof and a salt thereof can be produced as a recombinant protein by known genetic modification techniques or by methods using in vitro transcription-translation system. Alternatively, lipovitellin-1, a derivative thereof and a salt thereof can be purified from chicken egg yolk proteins.

Hereinafter, the term "peptide etc. of the present invention" encompasses lipovitellin-1, a derivative thereof and a salt thereof in addition to "the peptide of the present invention".

The peptide etc. of the present invention have been shown to exhibit the desired effects through oral administration to a mammal, and thus the above promoters, inhibitors and inducers are suitable for oral administration. The peptide etc. of the present invention, which are the egg yolk protein lipovitellin-1 or a fragment thereof, are highly safe and have mild effects, and thus can be administered or used for a long period of time.

Medicaments

The present invention provides a medicament comprising the peptide etc. of the present invention. Since the peptide etc. of the present invention have osteoblast growth-promoting activity, the peptide etc. can be used as a medicament for promoting bone formation. The medicament for promoting bone formation of the present invention can be suitable as a medicament for preventing or treating, for example, osteoporosis, osteogenesis imperfecta, hypercalcemia, hyperparathyroidism, osteomalacia, osteohalisteresis, osteolytic bone disease, osteonecrosis, Paget's disease, rheumatoid arthritis, bone loss due to osteoarthritis, inflammatory arthritis, osteomyelitis, glucocorticoid treatment, metastatic bone disease, periodontal bone loss, cancerous bone loss, age-related bone loss, fracture, and low back pain.

Since the peptide etc. of the present invention have chondrocyte growth-promoting activity and/or hyaluronic acid production-promoting activity, the peptide etc. can be used as a medicament for preventing or alleviating a cartilage disorder or a joint disease. Examples of the cartilage disorder include osteoarthritis, cartilage defects, cartilage injury, and meniscus injury. Examples of the joint disease include joint pain, rheumatoid arthritis, osteoarthritis, suppurative arthritis, gouty arthritis, traumatic arthritis, and degenerative joint disease.

The medicament of the present invention can be produced by appropriately blending the peptide etc. of the present invention as an active ingredient with a pharmaceutically acceptable carrier or additive in accordance with a known production method for pharmaceutical preparations (e.g., the methods described in the Japanese pharmacopoeia, etc.). In particular, the medicament may be, for example, an oral preparation or a parenteral preparation, including tablets (including sugar-coated tablets, film-coated tablets, sublingual tablets, orally disintegrating tablets, and buccal tablets), pills, powders, granules, capsules (including soft capsules and microcapsules), troches, syrups, liquids, emulsions, suspensions, controlled-release preparations (e.g., fast-release preparations, sustained release preparations, and sustained release microcapsules), aerosols, films (e.g., orally disintegrating films, and oral mucosal adhesive films), injections (e.g., subcutaneous injections, intravenous injections, intramuscular injections, and intraperitoneal injections), intravenous infusions, transdermal preparations, ointments, lotions, patches, suppositories (e.g., rectal suppositories and vaginal suppositories), pellets, transnasal preparations, transpulmonary preparations (inhalants), and eye drops. The amount of the carrier or additive to be added can be determined as appropriate based on the range typically used in the pharmaceutical field. The carrier or additive that may be added is not particularly limited and examples thereof include various types of carriers such as water, physiological saline, other aqueous solvents, and aqueous or oily vehicles; and various types of additives such as excipients, binders, pH adjusters, disintegrants, absorption promoters, lubricants, colorants, flavors and fragrances.

Examples of the additives that may be added to tablets, capsules, etc. include binders such as gelatin, corn starch, tragacanth, and gum arabic; excipients such as crystalline cellulose; swelling agents such as corn starch, gelatin, and alginic acid; lubricants such as magnesium stearate; sweeteners such as sucrose, lactose, and saccharin; and flavors such as peppermint flavor, wintergreen oil, and cherry flavor. When the unit dosage form is a capsule, a liquid carrier such as oils and fats can be further added in addition to the above types of materials. A sterile composition for injection can be prepared in accordance with a usual pharmaceutical practice (for example, by dissolving or suspending the active ingredient in a solvent such as water for injection or a natural vegetable oil). Aqueous liquids for injection that may be used are, for example, physiological saline and an isotonic solution containing glucose and/or other auxiliary substances (for example, D-sorbitol, D-mannitol, sodium chloride, etc.). The aqueous liquids for injection may be used in combination with an appropriate solubilizer, such as alcohols (e.g., ethanol), polyalcohols (e.g., propylene glycol, polyethylene glycol, etc.), and nonionic surfactants (e.g., polysorbate 80™, HCO-50, etc.). Oily liquids that may be used are, for example, sesame oil and soybean oil. The oily liquids may be used in combination with a solubilizer such as benzyl benzoate and benzyl alcohol. Other additives that may be added are, for example, buffering agents (e.g., a phosphate buffer, a sodium acetate buffer, etc.), soothing agents (e.g., benzalkonium chloride, procaine hydrochloride, etc.), stabilizers (e.g., human serum albumin, polyethylene glycol, etc.), preservatives (e.g., benzyl alcohol, phenol, etc.) and antioxidants.

The preparations produced in the above manner are safe and have low toxicity, and thus can be administered to, for example, humans and other mammals (e.g., rats, mice, rabbits, sheep, pigs, cows, cats, dogs, monkeys, etc.).

The amount of the peptide etc. of the present invention in the medicament of the present invention may vary with the dosage form, the administration method, the carrier to be used, etc., but is usually 0.01 to 100% (w/w), preferably 0.1 to 95% (w/w), relative to the total amount of the preparation. The medicament of the present invention containing the peptide etc. of the present invention in such an amount can be produced in accordance with a conventional method.

The dosage varies with the subject to which the medicament is to be administered, the symptom, the route of administration, etc., but in general, the dosage for oral administration to a human with a body weight of about 60 kg is about 0.01 to 1000 mg per day, preferably about 0.1 to 100 mg per day, and more preferably about 0.5 to 500 mg per day. The total daily dosage may be administered in a single dose or in divided doses.

The medicament of the present invention is expected to exhibit a high additive or synergistic effect in combination with another medicament for treating a bone disease or for treating a cartilage or joint disease. Said another medicament for promoting bone formation may be, for example, an active vitamin $D_3$ preparation, a vitamin K; preparation, a parathyroid hormone preparation (teriparatide), a female hormone preparation (estrogen), a bisphosphonate preparation, a SERM (raloxifene hydrochloride), a calcitonin preparation, etc. Said another medicament for treating a cartilage or joint disease may be, for example, glucosamine, chondroitin, type I collagen, type II collagen, N-acetylglucosamine, etc.

Food or Drink Products

The present invention provides a food or drink product comprising the peptide etc. of the present invention. The food or drink product of the present invention is suitable as a food or drink product for promoting bone formation and as a food or drink product for preventing and/or alleviating a cartilage disorder or a joint disease.

The food or drink product includes health foods, functional foods, foods for specified health use, and foods for sick people. The form of the food or drink product is not particularly limited and examples thereof include drinks such as tea drink, refreshing drink, carbonated drink, nutritional drink, fruit juice, and lactic drink; noodles such as buckwheat noodle, wheat noodle, Chinese noodle, and instant noodle; sweets and bakery products such as drop, candy, gum, chocolate, snack, biscuit, jelly, jam, cream, pastry, and bread; fishery and livestock products such as fish sausage, ham, and sausage; dairy products such as processed milk and fermented milk; fats, oils, and processed foods thereof, such as vegetable oil, oil for deep frying, margarine, mayonnaise, shortening, whipped cream, and dressing; seasonings such as sauce and dipping sauce; retort pouch foods such as curry, stew, rice-bowl cuisine, porridge, and rice soup; and frozen desserts such as ice cream, sherbet, and shaved ice.

The present invention also provides a supplement comprising the peptide etc. of the present invention. The supplement of the present invention is suitable as a supplement for promoting bone formation and as a supplement for preventing and/or alleviating a cartilage disorder or a joint disease. The supplement can be provided in the form of, for example, tablets, granules, powders or drinks.

The present invention provides a food additive comprising the peptide etc. of the present invention. The food additive of the present invention is suitable as a food additive for promoting bone formation and as a food additive for preventing and/or alleviating a cartilage disorder or a joint disease. The form of the food additive of the present invention is not particularly limited, and may be, for example, a liquid, a paste, a powder, flakes, granules, etc. The food additive of the present invention can be produced in accordance with a conventional production method for food additives.

Also provided is a feed or a feed additive comprising the peptide etc. of the present invention.

The present invention provides a cosmetic product comprising the peptide etc. of the present invention. The cosmetic product of the present invention is suitable as a cosmetic product for promoting bone formation and as a cosmetic product for preventing and/or alleviating a cartilage disorder or a joint disease. The cosmetic product includes the so-called medicated cosmetics (quasi drugs). Examples of the cosmetic product include washing lotions, shampoos, rinses, hair tonics, hair lotions, aftershave lotions, body lotions, makeup lotions, cleansing creams, massage creams, emollient creams, aerosol products, deodorizers, fragrances, deodorants, and bath fragrances. Depending on the purpose, the cosmetic product of the present invention may contain a component generally used in cosmetic products in addition to the peptide of the present invention, and such a component includes, for example, surfactants, moisturizers, animal- and plant-derived fats and oils, silicones, higher alcohols, lower alcohols, animal- and plant-derived extracts, ultraviolet absorbers, anti-inflammatories, sequestering agents, vitamins, antioxidants, thickeners, preservatives, bactericides, pH adjusters, colorants, and various fragrances.

The present invention further includes the following.

(a) Use of the peptide of the present invention or a derivative thereof or a salt thereof or lipovitellin-1 or a derivative thereof or a salt thereof for the production of a medicament for promoting bone formation or for preventing or alleviating a cartilage disorder or a joint disease.

(b) The peptide of the present invention or a derivative thereof or a salt thereof or lipovitellin-1 or a derivative thereof or a salt thereof for use in the promotion of bone formation or for the prevention or alleviation of a cartilage disorder or a joint disease.

(c) A method for promoting bone formation, the method comprising administering, to a mammal, an effective amount of the peptide of the present invention or a derivative thereof or a salt thereof or lipovitellin-1 or a derivative thereof or a salt thereof.

(d) A method for preventing or alleviating a cartilage disorder or a joint disease, the method comprising administering, to a mammal, an effective amount of the peptide of the present invention or a derivative thereof or a salt thereof or lipovitellin-1 or a derivative thereof or a salt thereof.

(e) A non-therapeutic method for promoting bone formation, the method comprising orally administering, to a mammal, the peptide of the present invention or a derivative thereof or a salt thereof or lipovitellin-1 or a derivative thereof or a salt thereof.

(f) A non-therapeutic method for preventing or alleviating a cartilage disorder or a joint disease, the method comprising orally administering, to a mammal, the peptide of the present invention or a derivative thereof or a salt thereof or lipovitellin-1 or a derivative thereof or a salt thereof.

(g) The peptide of the present invention or a derivative thereof or a salt thereof or lipovitellin-1 or a derivative thereof or a salt thereof for use in the promotion of bone formation or for the prevention or alleviation of a cartilage disorder or a joint disease.

(h) Use of the peptide of the present invention or a derivative thereof or a salt thereof or lipovitellin-1 or a derivative thereof or a salt thereof for the promotion of bone formation or for the prevention or alleviation of a cartilage disorder or a joint disease.

(i) Use of the peptide of the present invention or a derivative thereof or a salt thereof or lipovitellin-1 or a derivative thereof or a salt thereof for the production of a medicament for promoting bone formation or for preventing or alleviating a cartilage disorder or a joint disease.

EXAMPLES

The present invention will be described in more detail below with reference to Examples, but the present invention is not limited thereto.

Example 1

Identification of Active Substances for Promoting Growth of Osteoblasts in Egg-yolk Protein Hydrolysate (1) Preparation of Egg-yolk Protein Hydrolysate To 100 parts by mass of defatted egg yolk powder (Kewpie Corporation), 500 parts by mass of water was added, and the mixture was stirred until uniform. To the mixture, 5 parts by mass of "Alcalase" (trade name) (protease from *Bacillus licheniformis* (Novozymes Japan Ltd.)) was added, and the mixture was allowed to react at pH 7 at 55 to 60'C for 3 hours. At the end of the reaction, the enzyme was inactivated by heating at 90° C. for 10 minutes. Filtration was performed and the filtrate was collected. The filtrate was spray-dried to give an egg-yolk protein hydrolysate.

Instead of the defatted egg yolk powder as used above, a defatted egg yolk powder prepared from a commercially available egg yolk powder (e.g., a product produced by Kewpie Corporation) may be used. Specifically, 5 to 10 parts by mass of ethanol (or n-hexane) is added to 1 part by mass of a commercially available egg yolk powder, then the mixture is stirred with a blender for about 30 minutes and filtered, and the solid is collected. This procedure is repeated about 3 times for removal of the fat from the egg yolk. The defatted egg yolk is then air-dried to give a defatted dry powder.

(2) Measurement Method of Osteoblast Growth-promoting Activity

A mouse osteoblast-like cell line MC3T3-E1 Subclone-4 (ATCC No. CRL-2593) was cultured in α-MEM medium supplemented with 10% FBS at 5% $CO_2$ and 95% air at 37° C. until confluent. The cells were collected by trypsinization. The collected cells were suspended at $1 \times 10^4$ cells/mL in fresh α-MEM medium. One mL of the cell suspension was seeded in each well of a 24-well plate, and precultured at 5% $CO_2$ and 95% air at 37° C. On the next day, the medium was replaced with medium prepared by well mixing 50 µL of a sample or PBS (–) with 950 µL of fresh α-MEM medium supplemented with $CaCl_2$ to a Ca concentration of 500 µg/mL. The cells were further cultured for 72 hours. The growth activity of osteoblasts was measured by the cell counting method. The activity of the sample for promoting the growth of osteoblasts was expressed in terms of the relative value, with the growth rate in the PBS (–) group taken as 100.

(3) Fractionation with UF Membrane

In 600 mL of water, 60 g of the egg-yolk protein hydrolysate was dissolved. The solution was fractionated with a UF membrane (cut off molecular weight: 1 kDa, Nihon Millipore, Ltd.). Osteoblast growth-promoting activity was determined for a fraction with a molecular weight of 1 kDa or less and a fraction with a molecular weight of 1 kDa or more. As a positive control, the unfractionated egg-yolk protein hydrolysate (1 mg/mL) was used. The fraction with a molecular weight of 1 kDa or less and the fraction with a molecular weight of 1 kDa or more were used in amounts equal to the corresponding amounts in the unfractionated egg-yolk protein hydrolysate (i.e., the corresponding amounts in 0.2 mg of the egg-yolk protein hydrolysate).

The results are shown in FIG. 1. As is apparent from FIG. 1, the fraction with a molecular weight of 1 kDa or more showed osteoblast growth-promoting activity.

(4) Fractionation with Anion-exchange Column

The fraction with a molecular weight of 1 kDa or more, which showed osteoblast growth-promoting activity in the above (3), was further fractionated on an anion-exchange column (resin: Dowex, column size: 10 mm in diameter×63 mm) to give a flow-through fraction and fractions eluted with aqueous solutions with NaCl concentrations of 750 mM and 1 M. Osteoblast growth-promoting activity was determined for the fractions. As a positive control, the unfractionated egg-yolk protein hydrolysate (1 mg/mL) was used. The fractions were used in amounts equal to the corresponding amounts in the unfractionated egg-yolk protein hydrolysate (i.e., the corresponding amounts in 10 mg of the egg-yolk protein hydrolysate).

Figure 2:
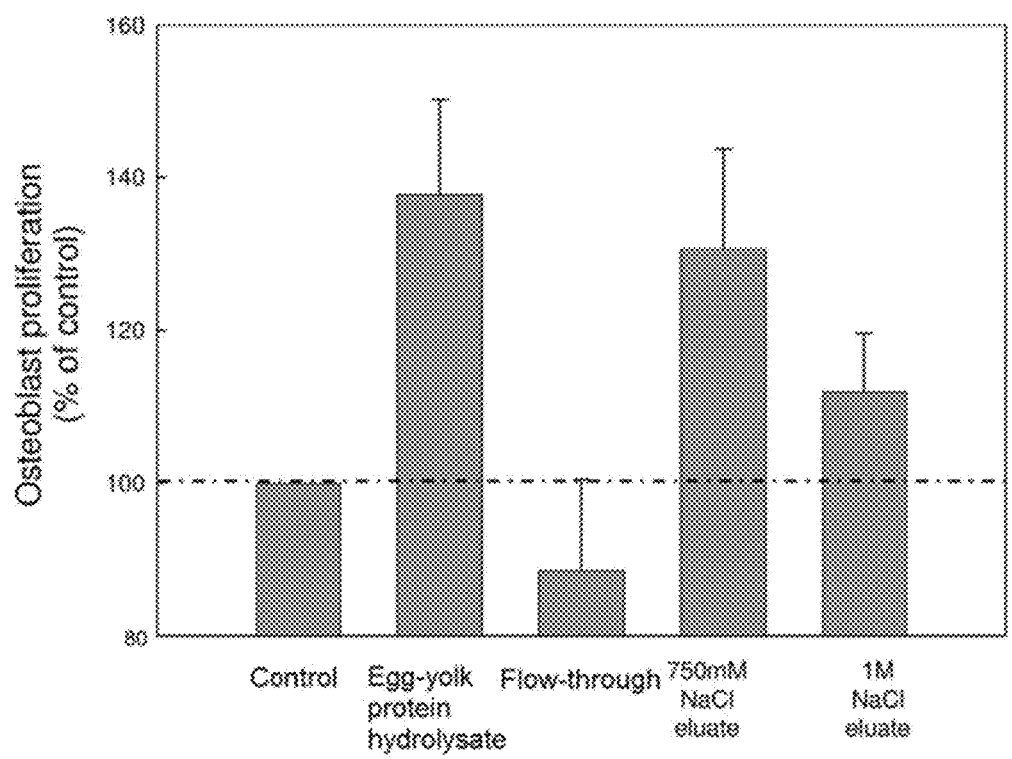
FIG. 2 shows a chart showing the measurement results of the osteoblast growth-promoting activity of a non-adsorbed fraction (flow-through) and fractions eluted with sodium chloride solutions at concentrations of 750 mM and 1 M from an anion-exchange column loaded with a fraction with a molecular weight of 1 kDa or more obtained from the egg-yolk protein hydrolysate.

The results are shown in FIG. 2. As is apparent from FIG. 2, the 750 mM NaCl eluate fraction showed the highest osteoblast growth-promoting activity.

(5) Fractionation by HPLC (First Round)

The 750 mM NaCl eluate fraction, which showed the highest osteoblast growth-promoting activity in the above (4), was further fractionated on a C18 reverse-phase column (column size: 50 mm in diameter×250 mm). The fractions were collected at 1 minute intervals from elution time zero to 45 minute. The HPLC conditions were as follows.

Figure 3:
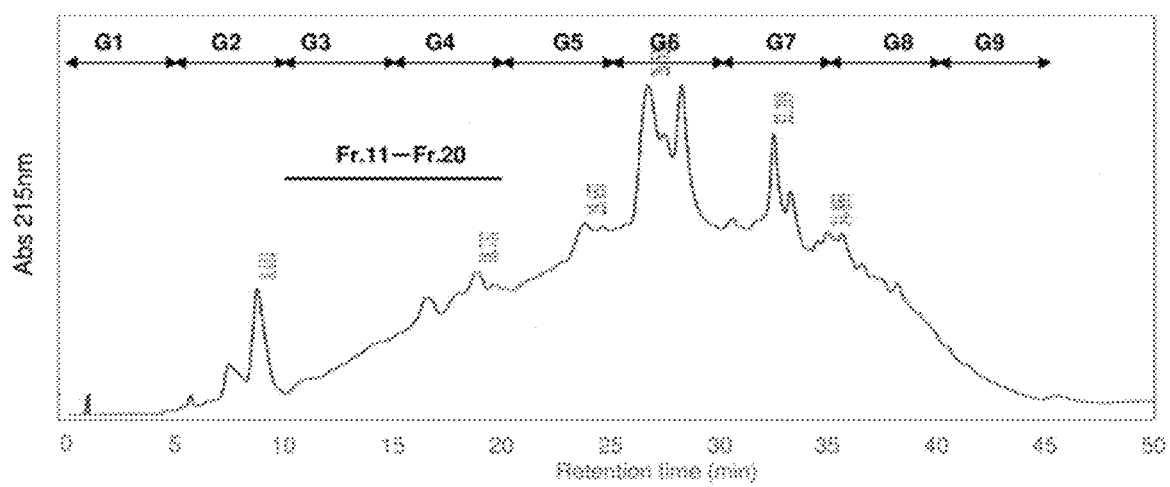
FIG. 3 is a chart showing fractions resulting from reverse-phase HPLC fractionation of the 750 mM NaCl eluate fraction, which showed high osteoblast growth-promoting activity.

Column: C18 reverse-phase column,
size: 50 mm in diameter×250 mm (HiPep Laboratories)
Mobile phase: (A) 10% acetonitrile/0.1% TFA
(B) 60% acetonitrile/0.1% TFA
B 5%→95% (40 min) gradient
Detection: UV 215 nm
Amount of samples: 601 mg In total, 45 fractions were collected, and every five fractions were combined to give G1 to G9 fractions (see FIG. 3). Osteoblast growth-promoting activity was determined for G1 to G9 fractions. The fractions were used in amounts equal to the corresponding amounts in the unfractionated egg-yolk protein hydrolysate (i.e., the corresponding amounts in 66 mg of the egg-yolk protein hydrolysate). As a positive control, the unfractionated egg-yolk protein hydrolysate (1 mg/mL) was used.

Figure 4:
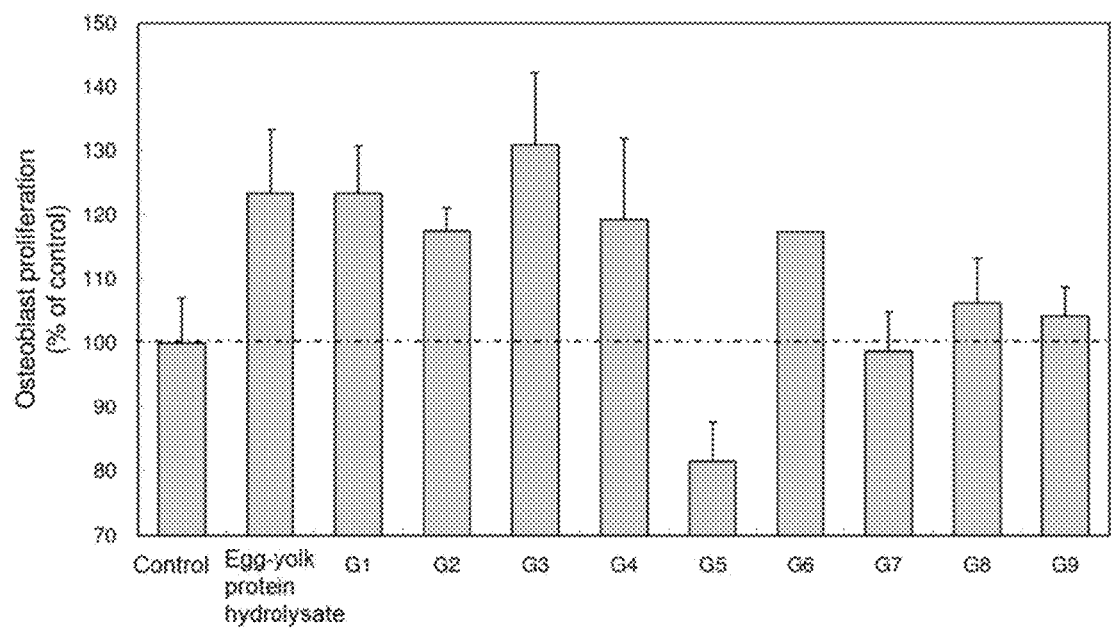
FIG. 4 is a chart showing the measurement results of the osteoblast growth-promoting activity of G1 to G9 indicated in FIG. 3.

The results are shown in FIG. 4. As is apparent from FIG. 4, G3 showed the highest osteoblast growth-promoting activity.

Osteoblast growth-promoting activity was further determined for the five fractions (fractions 11 to 15) of G3 and the five fractions (fractions 16 to 20) of G4. The fractions were used in amounts equal to the corresponding amounts in the unfractionated egg-yolk protein hydrolysate (i.e., the corresponding amounts in 66 mg of the egg-yolk protein hydrolysate). As a positive control, the unfractionated egg-yolk protein hydrolysate (1 mg/mL) was used.

Figure 5:
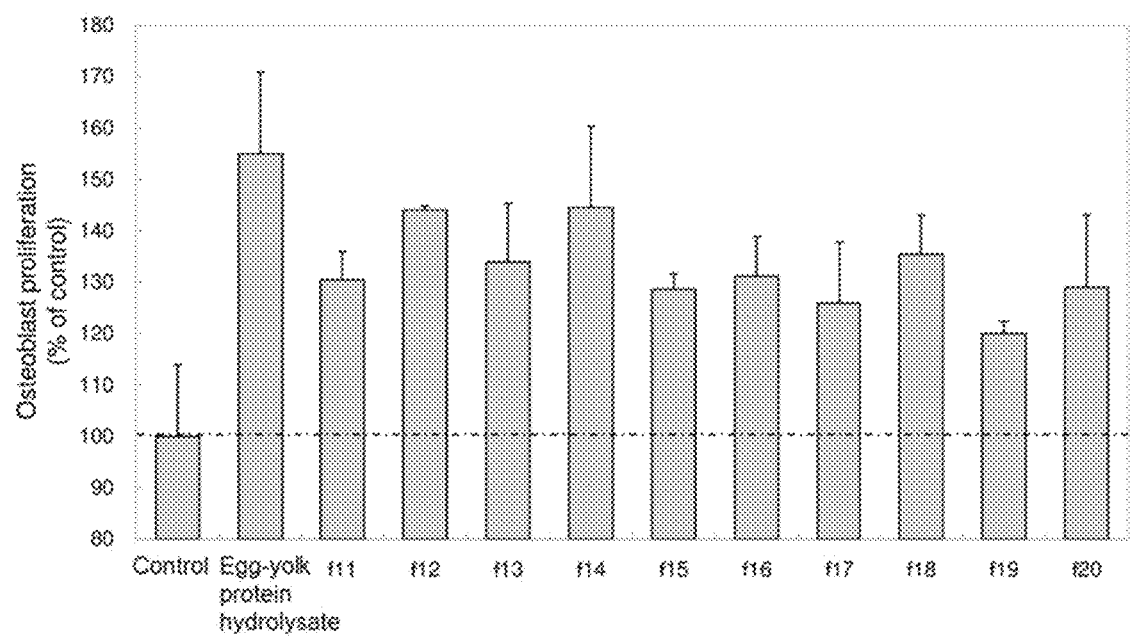
FIG. 5 is a chart showing the measurement results of the osteoblast growth-promoting activity of fractions 11 to 20 contained in G3 and G4.

The results are shown in FIG. 5. As is apparent from FIG. 5, all fractions 11 to 20 showed higher osteoblast growth-promoting activity than the control.

(6) Fractionation by HPLC (Second Round)

HPLC was performed on fractions 11 to 20 under the following conditions.

Figure 6:
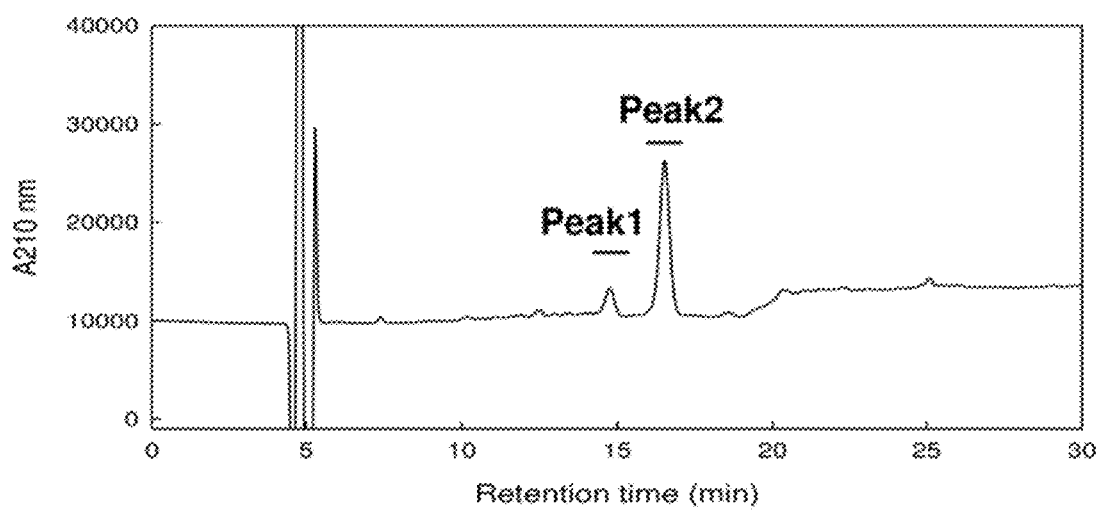
FIG. 6 is a chart showing peaks detected in fraction 12 by HPLC under conditions different from those of the above HPLC.

Column: ODS-A (trade name)(10×4.6 mm I.D.)
(YMC Co., Ltd.)
Mobile phase: 4% acetonitrile/0.1% TFA (isocratic)
Temperature: 40° C.
Detection: UV J 215 nm
Amount of samples: 50 µg Of fractions 11 to 20, two distinct peaks were detected in fraction 12 (see FIG. 6), and accordingly fraction 12 was further investigated. Briefly, fraction 12 was subjected to HPLC under the above conditions, and fractions with peak 1 and peak 2 were separated (see FIG. 6). Osteoblast growth-promoting activity was determined for the fraction with peak 1 (peak 1), the fraction with peak 2 (peak 2), and a fraction other than peak 1 and peak 2 fractions (Others). The fractions were used in amounts equal to the corresponding amounts in the unfractionated egg-yolk protein hydrolysate (i.e., the corresponding amounts in 133 mg of the egg-yolk protein hydrolysate). As a positive control, the unfractionated egg-yolk protein hydrolysate (1 mg/mL) was used.

Figure 7:
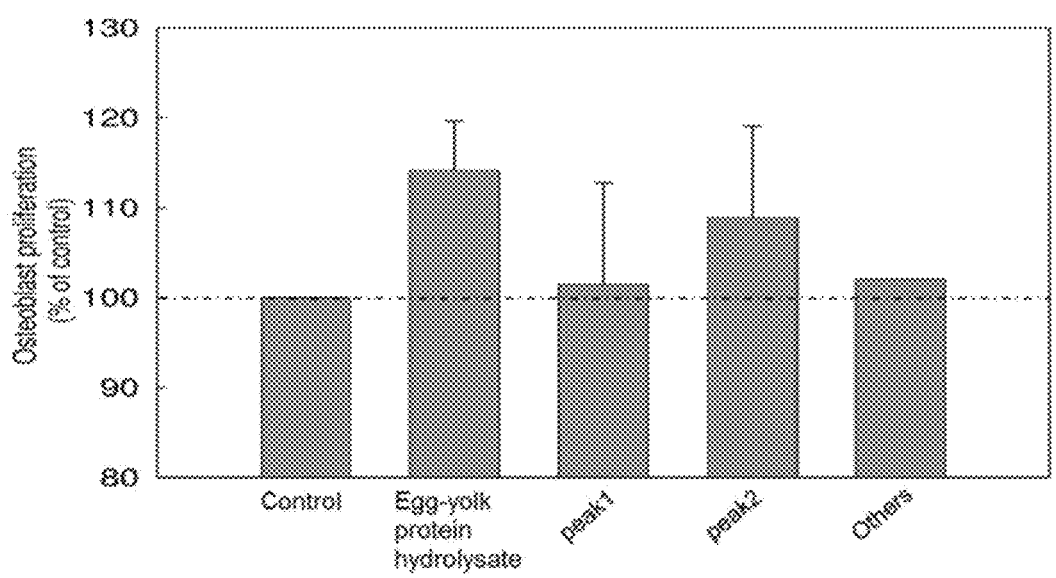
FIG. 7 is a chart showing the measurement results of the osteoblast growth-promoting activity of fractions with the two peaks indicated in FIG. 6.

The results are shown in FIG. 7. As is apparent from FIG. 7, the fraction with peak 2 showed the highest osteoblast growth-promoting activity.

(7) Identification of Peptides

The amino acid sequences of the peptides contained in the fraction with peak 2 were analyzed using MALDI-TOF-MS (mass spectrometer). The analysis results revealed that at least six types of peptides were contained in the fraction with peak 2 as shown in FIG. 8. These peptides are fragments of lipovitellin-1 contained in egg yolk, and each correspond to the following positions in the amino acid sequence of lipovitellin-1 (SEQ ID NO: 8): No. 1, positions 1045-1052; No. 2, positions 1045-1051; No. 3, positions 1047-1051; No. 4, positions 1053-1059; No. 5, positions 1052-1059; and No. 6, positions 1045-1059.

Example 2

Study of Osteoblast Growth-promoting Activity of Synthetic Peptides

The six types of peptides shown in Example 1 to have osteoblast growth-promoting activity were chemically synthesized and their osteoblast growth-promoting activities were determined. The peptide synthesis was performed with a SyroII automatic peptide synthesizer (Biotage Japan Ltd.).

Osteoblast growth-promoting activity was determined for the synthetic peptides in the same manner as in Example 1. The synthetic peptides were added at 2.5, 5 or 10 µg/mL per well. As a control, PBS (−) was added. The osteoblast growth-promoting activity was expressed in terms of the relative value, with the growth rate in the PBS (−) group taken as 100.

Figure 9:
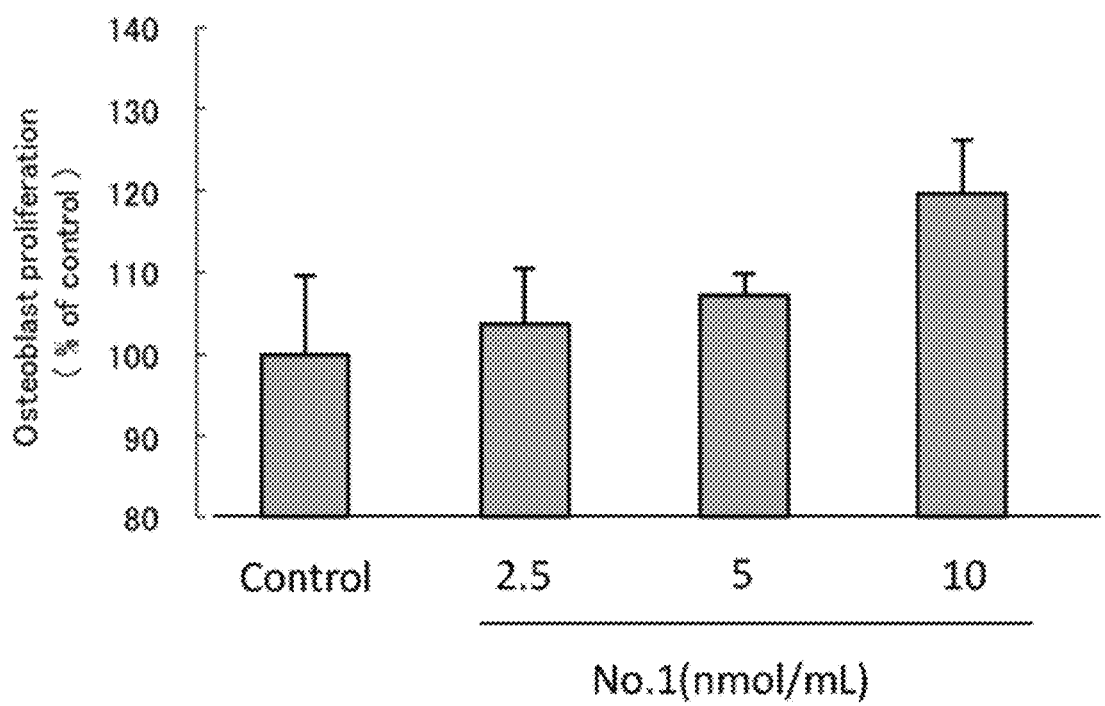
FIG. 9 is a chart showing the measurement results of the osteoblast growth-promoting activity of a synthetic peptide (No. 1).
Figure 11:
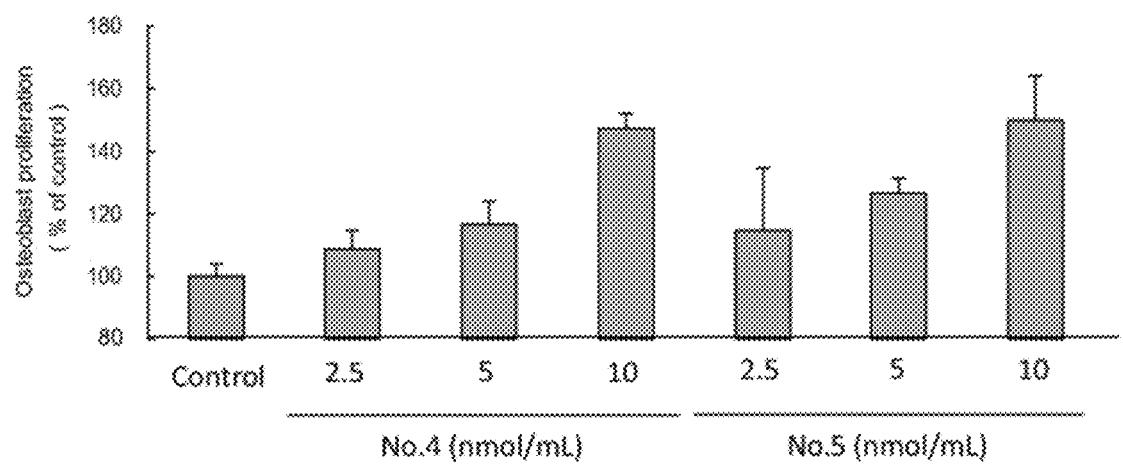
FIG. 11 is a chart showing the measurement results of the osteoblast growth-promoting activity of synthetic peptides (No. 4 and No. 5).
Figure 12:
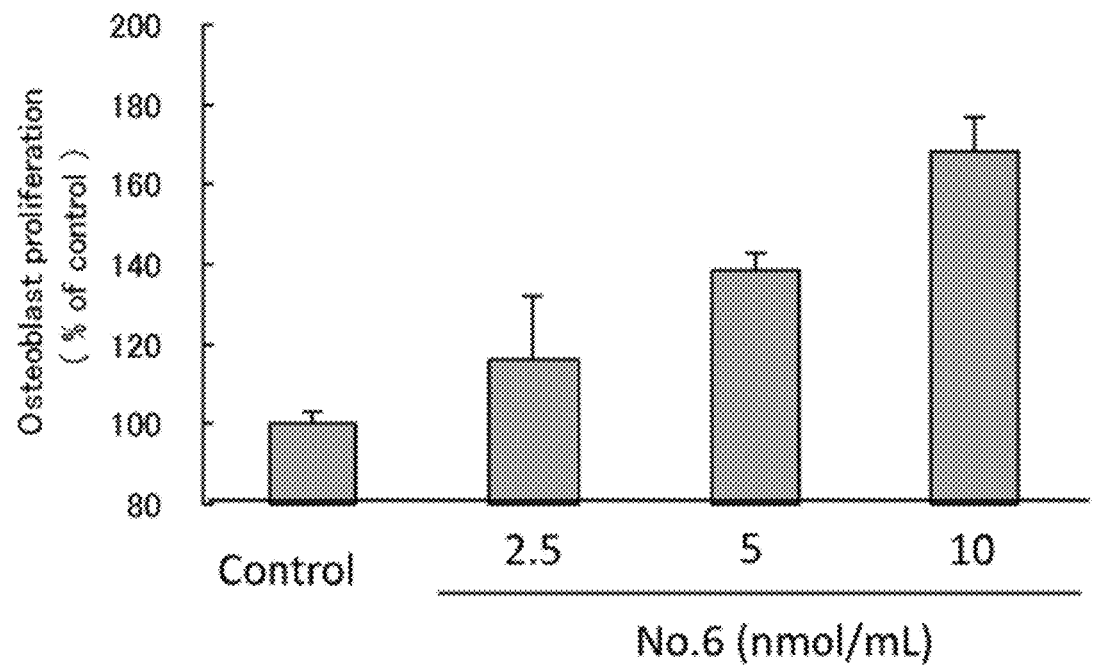
FIG. 12 is a chart showing the measurement results of the osteoblast growth-promoting activity of a synthetic peptide (No. 6).

FIG. 9 shows the results of No. 1, FIG. 10 shows the results of No. 2 and No. 3, FIG. 11 shows the results of No. 4 and No. 5, and FIG. 12 shows the results of No. 6. As is apparent from FIGS. 9 to 12, all the synthetic peptides promoted the growth of osteoblasts in a concentration-dependent manner.

Example 3

Study of Bone Growth Promoting Effect of Synthetic Peptides in Adolescent Rats

One of the synthetic peptides (No. 1) or physiological saline (control) was administered to Sprague-Dawley male rats at three weeks old by oral gavage using a gastric tube once a day for four days. The dose of the synthetic peptide was 1, 10 or 100 mg/kg·day. As a positive control, human growth hormone (hGH) (Norditropin, Standard Commodity Classification No. of Japan: 872412) was subcutaneously administered at 20 µg/kg·day once a day for four days. After the administration on day 4, calcein was subcutaneously administered, and the rats were kept for one day. The rats were euthanized by bloodletting under anesthesia, and the tibiae were harvested. The tissue specimens of the tibial growth plates were prepared, and calcein deposition areas (fluorescent regions) on the tibial growth plates were measured under a fluorescent microscope to determine the longitudinal bone growth.

Figure 13:
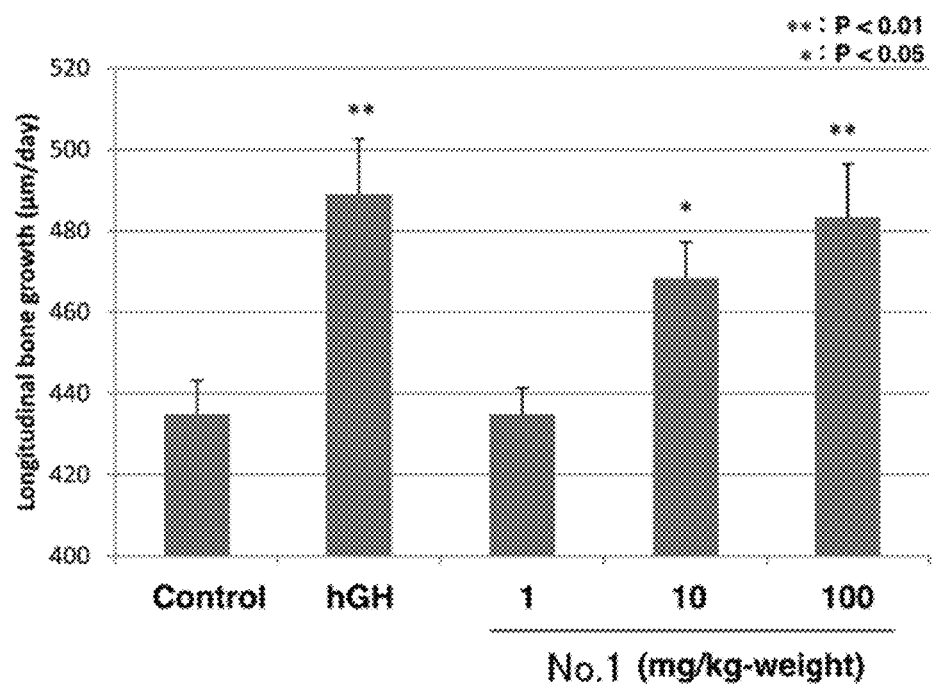
FIG. 13 is a chart showing the measurement results of the increased height of the tibial growth plates of rats after oral administration of a synthetic peptide (No. 1).

The results are shown in FIG. 13. As is apparent from FIG. 13, the increase in the height of the tibial growth plates was enhanced in a manner consistent with the increase in the dose of the synthetic peptide. The effect of enhancing the increase in the height by the synthetic peptide at the highest dose was comparable to the effect of the subcutaneous administration of the human growth hormone. The results revealed that oral administration of the peptides of the present invention promotes bone formation.

Example 4

Study of Chondrocyte Growth-promoting Activity of Synthetic Peptides

This study was performed using mouse-derived chondrogenic cell line ATDC5 (RIKEN BANK, RBC0565). ATDC5 cells in the logarithmic growth phase were suspended at $3\times10^4$ cells/mL in Eagle MEM medium supplemented with 5% FCS (fetal calf serum), and 100 µL of the cell suspension was seeded in each well of a 96-well plate and precultured at 5% $CO_2$ and 95% air at 37° C. On the next day, the medium in each well was removed, and medium containing the synthetic peptide (No. 1 or No. 6) at 10 nmol/mL was added. The cells were cultured for 72 hours. As a control, medium without a synthetic peptide was added. The reaction solution (10 µg/well) of Cell Counting Kit-8 (Dojindo Laboratories) was added to each well. The plate was incubated for 3 hours, and the absorbance at 450 nm was measured with a microplate reader. The activity of the synthetic peptides for promoting the growth of chondrocytes was expressed in terms of the relative value, with the absorbance (growth rate) in the control group taken as 100%.

Figure 14:
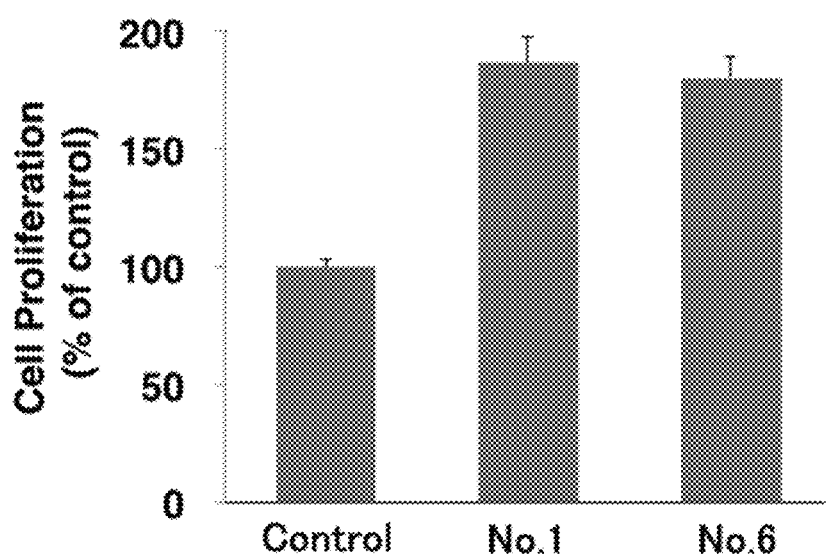
FIG. 14 is a chart showing the measurement results of the chondrocyte growth-promoting activity of synthetic peptides (No. 1 and No. 6).

The results are shown in FIG. 14. As is apparent from FIG. 14, synthetic peptide No. 6 and synthetic peptide No. 1 (a fragment of No. 6) showed chondrocyte growth-promoting effect.

Example 5

Study of Hyaluronic Acid Production-promoting Activity of Synthetic Peptides

This study was performed using the mouse-derived cell line ATDC5 as used in Example 4. ATDC5 cells in the logarithmic growth phase were seeded at $2\times10^4$ cells/mL per well in a 24-well plate containing DMEM/F-12 (1:1) medium supplemented with 5% FCS (fetal calf serum), 10 µg/mL transferrin and $3\times10^{-8}$ M sodium selenite. The cells were precultured at 5% $CO_2$ and 95% air at 37° C. On the next day, the medium in each well was removed, and medium containing the synthetic peptide (No. 1 or No. 6) at 10 nmol/mL was added. The cells were cultured for 72 hours. As a control, medium without a synthetic peptide was added. After 48 hours of culture, the culture supernatants were collected, and their hyaluronic acid concentrations were measured using QnE Hyaluronic Acid ELISA Assay (Biotech Trading Partners). The concentrations of hyaluronic acid in the culture supernatants of the synthetic peptide addition group were calculated by subtracting the absorbance of the background from the absorbance of the supernatants, and fitting the resulting values to the reference curve prepared using the standard.

Figure 15:
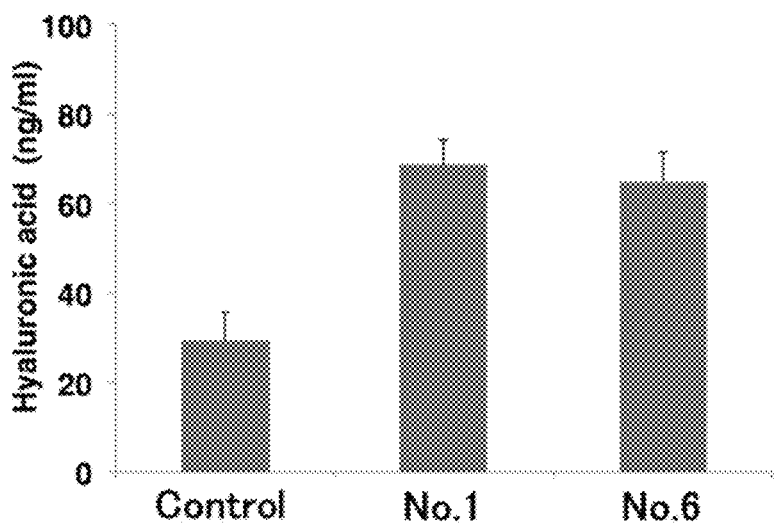
FIG. 15 is a chart showing the measurement results of the hyaluronic acid production-promoting activity of synthetic peptides (No. 1 and No. 6).

The results are shown in FIG. 15. As is apparent from FIG. 15, synthetic peptide No. 6 and synthetic peptide No. 1 (a fragment of No. 6) showed hyaluronic acid production-promoting effect.

Example 6

Bone Density Recovery Test Using Synthetic Peptides

Sprague-Dawley male rats at three weeks old were initially fed with a low-calcium diet (containing 0.05% calcium carbonate) for one week, and then fed with a normal diet (containing 1.2% calcium carbonate). The synthetic peptide (No. 1) or physiological saline (control) was administered to the rats by oral gavage using a gastric tube once a day for seven days. The dose of the synthetic peptide was 1, 10 or 100 mg/kg·day. After the oral administration on day 7, the rats were euthanized by bloodletting under anesthesia, and the femurs and tibiae were harvested. The bone volume and bone morphology of the tibiae and femurs were measured by dual energy x-ray absorptiometry (DXA) and peripheral quantitative computed tomography (pQCT). The results revealed that the length, weight, and bone density of the tibiae tended to be higher in the synthetic peptide administration group than in the control group, indicating that the synthetic peptide promoted the recovery of the bone density loss due to calcium deficiency.

Example 7

Study Using Postmenopausal Osteoporosis Model of Ovariectomized Rats

Female rats (eight months old, ten rats in each group) underwent ovariectomy (OVX), and synthetic peptide No. 1 was administered to the rats by oral gavage using a gastric tube once a day from the first postoperative day for six months. The dose of the synthetic peptide was 1, 10 or 100 mg/kg·day. The results revealed that the OVX-synthetic peptide administration group showed an increase in the bone density of the distal femoral metaphysis in a manner consistent with the increase in the dose of the synthetic peptide, and the increase was significant as compared with the OVX-control group (non-synthetic peptide administration group). The medium-dose administration group (10 mg/kg·day) and the high-dose administration group (100 mg/kg·day) showed an equal or higher bone density as compared with the sham operation group without removal of the ovary. Regarding the measured bone morphology parameters, the cancellous bone volume in the proximal tibial metaphysis increased in the OVX-synthetic peptide administration group in a manner consistent with the increase in the dose, and the increase was significant as compared with the OVX-control group. The medium-dose administration group and the high-dose administration group showed an equal or higher volume of the cancellous bone as compared with the sham operation group without removal of the ovary. OVX-induced reduction in the trabecular numbers and the trabecular width and OVX-induced increase in the trabecular separation tended to be inhibited in the OVX-synthetic peptide administration group.

Example 8

Bone Formation-promoting Effect in Mature and Aged Rats

Synthetic peptide No. 1 was administered to mature female rats (eight months old, ten rats in each group) by oral gavage using a gastric tube once a day for 20 weeks. The dose of the synthetic peptide was 1, 10 or 100 mg/kg·day. As a positive control, alendronate sodium hydrate (hereinafter called "alendronate") (300 µg/kg) was subcutaneously administered once a day for 20 weeks. The results revealed that the bone density in the femurs and the cancellous bone volume in the proximal tibial metaphysis at the end of the administration were significantly increased in the synthetic peptide administration group and the alendronate administration group as compared with the control group. The levels of the increases in the synthetic peptide administration group were comparable to those in the alendronate administration group.

Synthetic peptide No. 1 was administered to aged female rats (13 to 14 months old, ten rats in each group) by oral gavage using a gastric tube once a day for 20 weeks. The dose of the synthetic peptide was 1, 10 or 100 mg/kg·day. As a positive control, the alendronate (300 µg/kg) was subcutaneously administered once a day for 20 weeks. The results revealed that the bone density in the femurs and the cancellous bone volume in the proximal tibial metaphysis increased in a dose-dependent manner in the synthetic peptide administration group.

Example 9

Inhibitory Effect on Bone Resorption in Osteoclast Culture System

A crude fraction of osteoclasts was prepared from the long bones and scapulae of rabbits. The crude fraction was cultured on dentine slices in the presence of the synthetic peptides (0.0001 to 1000 µmol/L) for 48 hours, resulting in a reduction in the total area of pits in a concentration-dependent manner. Isolated osteoclasts were also prepared by collagen treatment of the crude fraction of osteoclasts. The isolated osteoclasts were pretreated with the synthetic peptides (0.0001 to 1000 µmol/L) for 15 minutes and then cultured on dentine slices for 24 hours, resulting in a reduction in the total area of pits in a concentration-dependent manner.

Example 10

Study of Activity of Synthetic Peptides for Promoting the Growth of Mesenchymal Stem Cells Mouse mesenchymal stem cells 10T½ (JCRB accession No. JCRB9080) or ST2 (Riken BRC ID: RCB0224) were seeded at 5000 cells/well in a 96-well plate containing DMEM medium supplemented with 10% fetal bovine serum. The synthetic peptides were added to the wells at 0.1 to 100 nmol/mL, and the cells were cultured for 72 hours. Cell Counting Kit-8 (Dojindo Laboratories) was added at 10 µL/100 µL medium, and the plate was incubated at 37° C. for 1 to 4 hours. The absorbance at 450 nm was measured with a microplate reader. The results revealed that the addition of the synthetic peptides significantly increased the growth of 10T½ and ST2 cells.

Example 11

Study of Activity of Synthetic Peptides for Inducing Differentiation of Mesenchymal Stem Cells Mouse mesenchymal stem cells 10T½ or ST2 were seeded at 5000 cells/well in a 96-well plate containing DMEM medium supplemented with 10% fetal bovine serum. The synthetic peptides were added to the wells at 0.1 to 100 nmol/mL, and the cells were cultured for four days. The medium was replaced with DMEM medium supplemented with β-glycerophosphoric acid I (10 mM) and ascorbic acid (50 µg/mL). At this medium replacement, medium with or without the synthetic peptides was used for the examination of the effect of their presence. The cells were further cultured in the medium for three days (in total, seven days of culture). The cells were fixed, and stained for alkaline phosphatase activity using Alkaline Phosphatase Substrate Kit I (VECTOR Red) (Vector Laboratories). The results indicated strong alkaline phosphatase activity in the cells cultured in the presence of the synthetic peptides. The cells cultured in the absence of the synthetic peptides did not show such activity. That is, it was revealed that the addition of the synthetic peptides efficiently induced differentiation of undifferentiated mesenchymal stem cells into osteoblast-like cells (osteogenic cells) over a relatively short period of time of four days.

Example 12

Study of Activity of Synthetic Peptides for Inducing Differentiation of Chondrogenic Cells Mouse EC (embryonic carcinoma)-derived cloned cell line ATDC5 (Riken BRC ID: RCB0565) with a potential to differentiate into chondrocytes was cultured in DMEM/F-12 medium supplemented with 5% FBS. The ATDC cells were seeded at $2 \times 10^4$ cells/well in a 48-well plate. After 24 hours of culture, the culture supernatant was removed, then DMEM/F-12 medium supplemented with 10 ng/mL insulin was added, and the synthetic peptides were added at 0.1 to 100 nmol/mL. As a positive control, 1 and 5 ng/mL BMP-2 or BMP-4 (R&D) was used. The medium was changed every 3 to 4 days.

In order to investigate whether the synthetic peptides have a synergistic effect with BMP-2 or BMP-4, co-addition of the synthetic peptides at 0.1 to 100 nmol/mL with BMP-2 or BMP-4 at 1 ng/mL was performed. The cells were cultured for 14 days with periodical medium replacement. The cells were fixed in 10% formalin neutral buffer, and stained with Alcian-blue solution for 4 hours. After washing off the dye, the plate was dried and photographed.

The results revealed that the mouse chondrogenic cells ATDC5 formed Alcian-blue-positive nodules by addition of the synthetic peptides, and the number of the nodules increased in a concentration-dependent manner. This fact indicated that the synthetic peptides induced the differentiation of the ATDC5 cells into chondrocytes. The synergistic effect with BMP-2 or BMP-4 was also indicated.

Example 13

Analysis of Bone Formation Factors in Osteoblast-like Cells

Mouse osteoblast-like cell line MC3T3-E1 Subclone-4 (ATCC No. CRL-2593) was cultured at 5% $CO_2$ and 95% air at 37° C. for 72 hours in 10% FBS-containing α-MEM medium with the addition of the synthetic peptides at 2.5, 5, or 10 µg/mL. After the end of culture, the alkaline phosphatase (ALP) activity of the osteoblast-like cells was measured by the p-nitrophenyl phosphate substrate method. The levels of osteocalcin (OCN) in the culture supernatants were determined by ELISA using an osteocalcin measurement kit (Takara Bio). The results indicated that the ALP activity and the OCN level had a tendency to increase depending on the concentration of the synthetic peptides added. ALP and OCN are considered to be the factors reflecting bone formation function, and thus the results suggested that the synthetic peptides promote the bone formation function of osteoblast-like cells via such related factors.

Example 14

Figure 16:
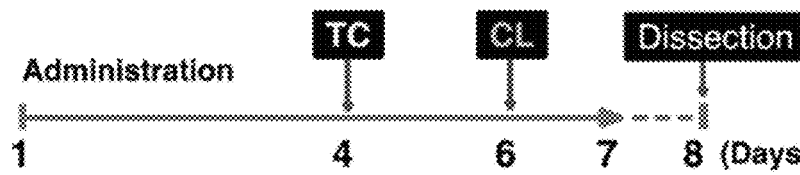
FIG. 16 shows the experimental protocol of Example 14.

Study of Effect of Synthetic Peptides for Promoting Bone Formation in Growth Cartilage and Primary Cancellous Bone One of the synthetic peptides (No. 1) or water for injection (control) was administered to Crlj:W1 male rats at four weeks old by oral gavage using a gastric tube once a day for seven days (n=3 in each group). The dose of the synthetic peptide (No. 1) was 100 mg/kg-day. As a positive control, human growth hormone (hGH) (Norditropin, Standard Commodity Classification No. of Japan: 872412) was subcutaneously administered at 500 µg/kg-day once a day for seven days. As fluorescent labels for the site of bone formation, tetracycline (20 mg/kg) was subcutaneously administered on day 4 after the administration of the peptide or control, and then calcein (10 mg/kg) was subcutaneously administered on day 6 after the administration of the peptide or control. After the administration of the test sample on day 7, the rats were kept under fasting conditions. Twenty-four hours later, the blood was collected. The rats were then euthanized by bloodletting under anesthesia, and the tibiae were harvested (see FIG. 16). Non-decalcified specimens of the proximal tibiae were prepared and photographed under a fluorescent microscope (BX-53, OLYMPUS). The bone morphology was measured using a morphometry system (Histometry RT digitizer, System Supply Co., Ltd.) and an analysis software (CSS-840 cancellous bone morphometry version, System Supply Co., Ltd.). The longitudinal growth rate (Lo.G.R.) in the growth cartilage, which is the increase in the height per day, was determined by measuring the distance between the tetracycline label and the calcein label, and dividing the distance by the administration interval between the fluorescent labels (two days).

Figure 17:
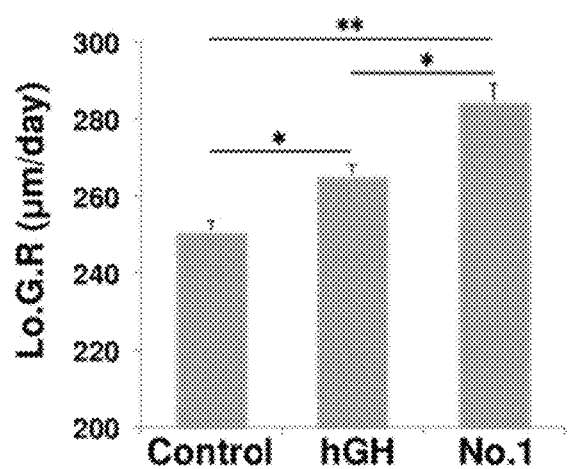
FIG. 17 is a chart showing the measurement results of the growth rate of the growth cartilage per day (in the longitudinal direction) in a synthetic peptide administration group.
Figure 18:
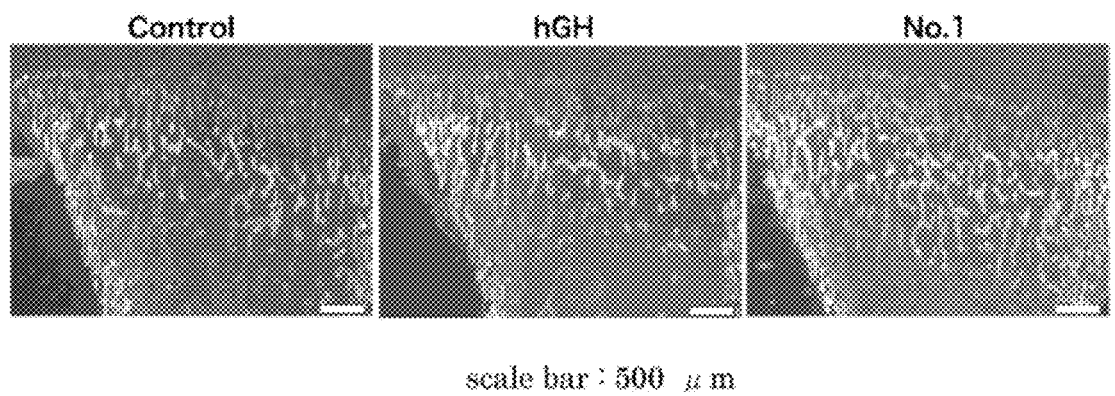
FIG. 18 shows fluorescent microscope images of the formation of primary cancellous bone in a synthetic peptide administration group.

The results revealed that the hGH administration group and the No. 1 administration group showed significant promotion of bone growth as compared with the control group, and that the bone growth-promoting effect observed in the No. 1 administration group was significant as compared with the hGH administration group (FIG. 17). The No. 1 administration group also showed a high frequency of incorporation of the fluorescent labels into the primary cancellous bone as compared with the control group and the hGH administration group, suggesting that the synthetic peptide induced fast formation of the cancellous bone in the growth phase (FIG. 18, white region).

Figure 19:
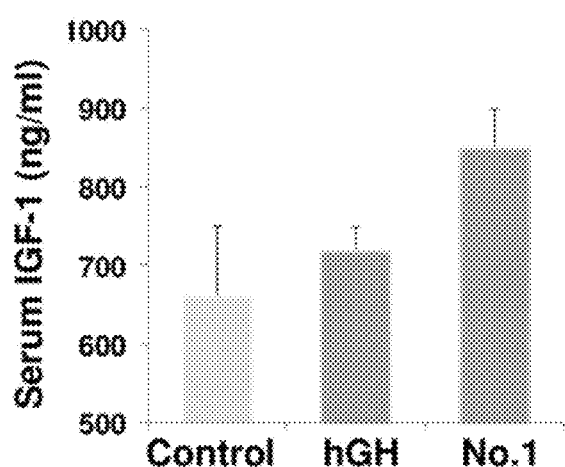
FIG. 19 is a chart showing an increase in the serum level of insulin-like growth factor (IGF-1) in a synthetic peptide administration group.

The measurement of the serum level of insulin-like growth factor (IGF-1) by ELISA (Mouse/Rat IGF-I Quantikine ELISA Kit (MG100), R&D Systems, Inc.) revealed that the IGF-1 levels in the hGH administration group and the No. 1 administration group were higher than that in the control group (FIG. 19). The increase in the level of IGF-1, which is related to growth of the bones and muscles in a growth phase, may contribute to the bone growth-promoting effect.

It is apparent from the above results that oral administration of the peptides of the present invention promotes longitudinal bone growth and the formation of the cancellous bone, which is the internal structure of the bone.

Example 15

Figure 20:
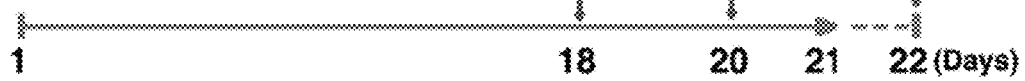
FIG. 20 shows the experimental protocol of Example 15.

Study of Effect of Synthetic Peptides for Promoting Bone Formation in Growth Cartilage and Secondary Cancellous Bone One of the synthetic peptides (No. 1) or water for injection (control) was administered to Crlj:W1 male rats at four weeks old by oral gavage using a gastric tube once a day for 21 days (n=3 in each group). The dose of the synthetic peptide was 100 mg/kg·day. As a positive control, human growth hormone (hGH) (Norditropin, Standard Commodity Classification No. of Japan: 872412) was subcutaneously administered at 500 μg/kg·day once a day for 21 days. As fluorescent labels for the site of bone formation, tetracycline (20 mg/kg) was subcutaneously administered on day 18 after the administration of the peptide or control, and then calcein (10 mg/kg) was subcutaneously administered on day 20 after the administration of the peptide or control. After the administration of the test sample on day 21, the rats were kept under fasting conditions. Twenty-four hours later, the rats were euthanized by bloodletting under anesthesia, and the tibiae were harvested (see FIG. 20). Non-decalcified specimens of the proximal tibiae were prepared and photographed under a fluorescent microscope (BX-53, OLYMPUS). The bone morphology was measured using a morphometry system (Histometry RT digitizer, System Supply Co., Ltd.) and an analysis software (CSS-840 cancellous bone morphometry version, System Supply Co., Ltd.). The longitudinal growth rate (Lo.G.R.) in the epiphyseal cartilage, which is the increase in the height per day, was determined by measuring the distance between the tetracycline label and the calcein label, and dividing the distance by the administration interval between the fluorescent labels (two days).

Figure 21:
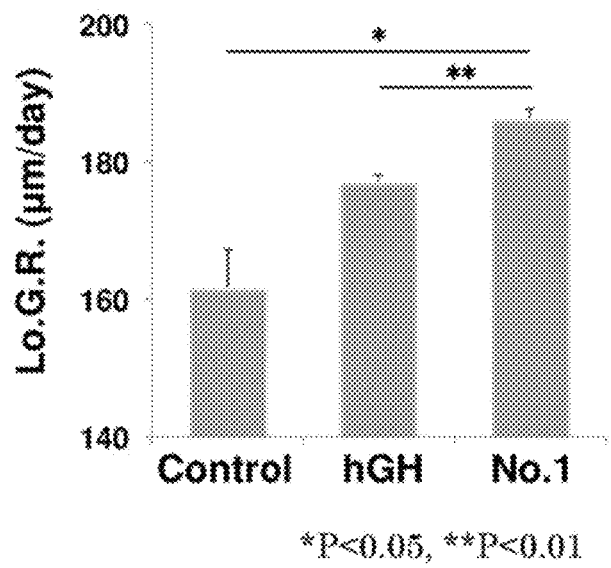
FIG. 21 is a chart showing the calculation results of the increased height of the rat tibiae per day in a synthetic peptide administration group.

The results revealed that the hGH administration group and the No. 1 administration group showed significant promotion of bone growth as compared with the control group, and that the bone growth-promoting effect observed in the No. 1 administration group was significant as compared with the hGH administration group (FIG. 21). It was thus indicated that long-term oral administration of the peptides of the present invention also promotes longitudinal bone growth.

Figure 22:
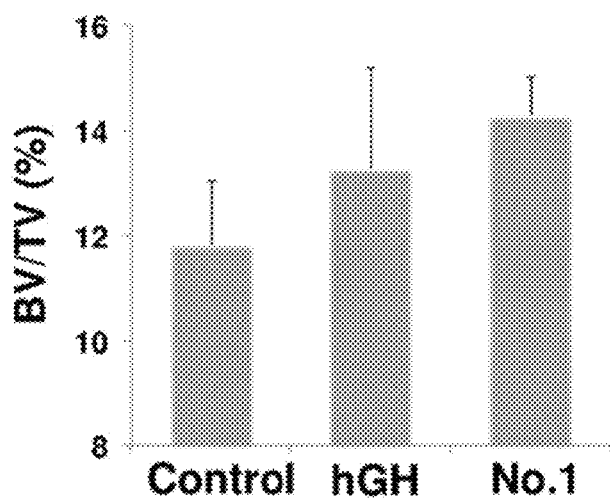
FIG. 22 is a chart showing the measurement results of the secondary cancellous bone volume relative to the bone tissue volume in rats in a synthetic peptide administration group.
Figure 23:
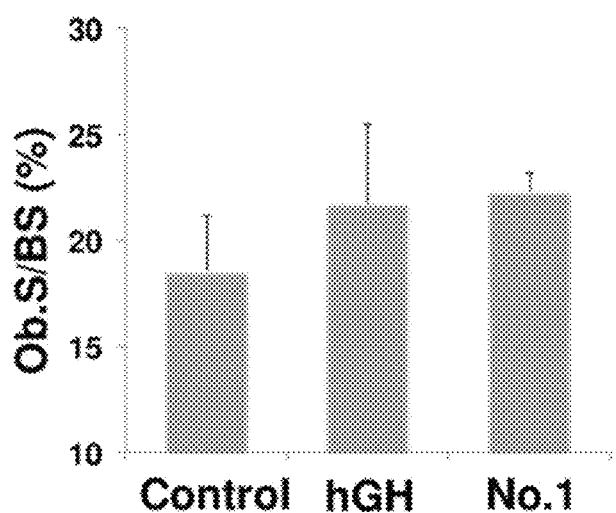
FIG. 23 is a chart showing the measurement results of the percentage of the bone surface occupied by osteoblasts relative to the total bone surface in a synthetic peptide administration group.
Figure 24:
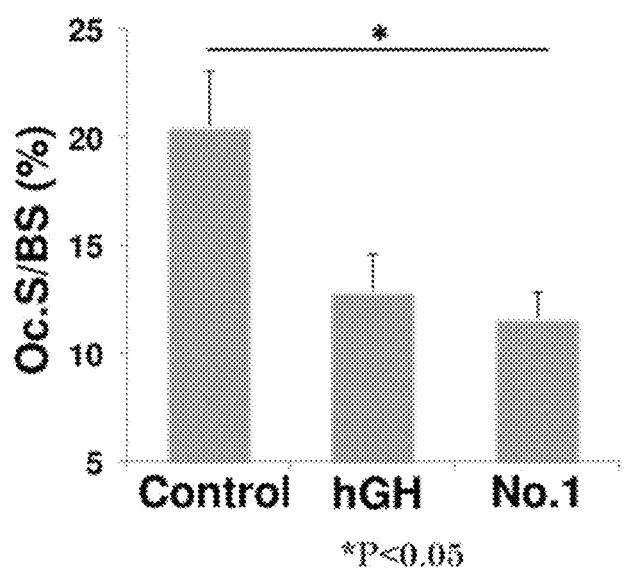
FIG. 24 is a chart showing the measurement results of the percentage of the bone surface occupied by osteoclasts relative to the total bone surface in a synthetic peptide administration group.
Figure 25:
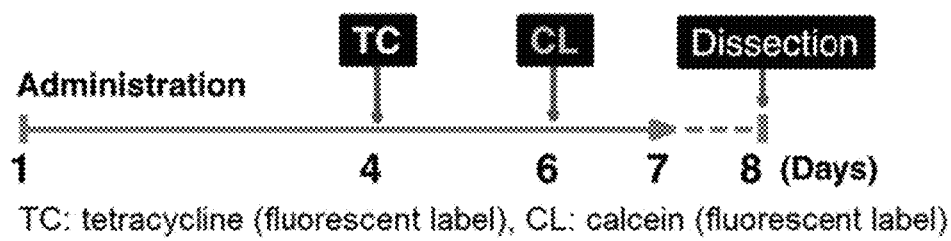
FIG. 25 shows the experimental protocol of Example 16.

The analysis of the secondary cancellous bone volume (bone volume/tissue volume (BV/TV)) by the above analysis system revealed that the No. 1 administration group had a higher secondary cancellous bone volume than the control group and the hGH administration group (FIG. 22). The No. 1 administration group also showed a high percentage of the bone surface occupied by osteoblasts relative to the total bone surface (osteoblast surface/bone surface (Ob.S/BS)) (FIG. 23) and a low percentage of the bone surface occupied by osteoclasts relative to the total bone surface (osteoclast surface/Bone surface (Oc.S/BS)) (FIG. 24).

It is apparent from the above results that oral administration of the peptides of the present invention potentially induces skeletal metabolism in which bone formation is dominant via an increase of osteoblasts and inhibition of differentiation into osteoclasts.

Example 16

Figure 26:
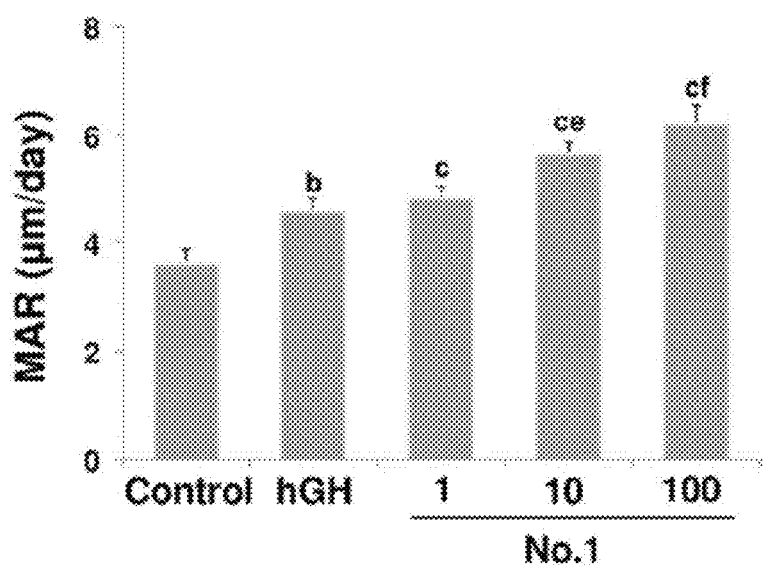
FIG. 26 is a chart showing the calculation results of the mineral apposition rate, per day, in the secondary cancellous bone of rats in a synthetic peptide administration group.
Figure 27:
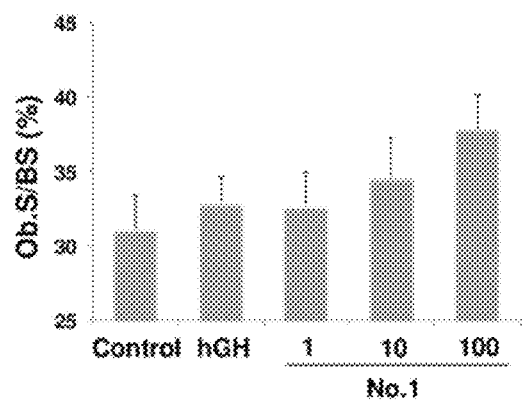
FIG. 27 is a chart showing the measurement results of the percentage of the bone surface occupied by osteoblasts relative to the total bone surface in a synthetic peptide administration group.
Figure 28:
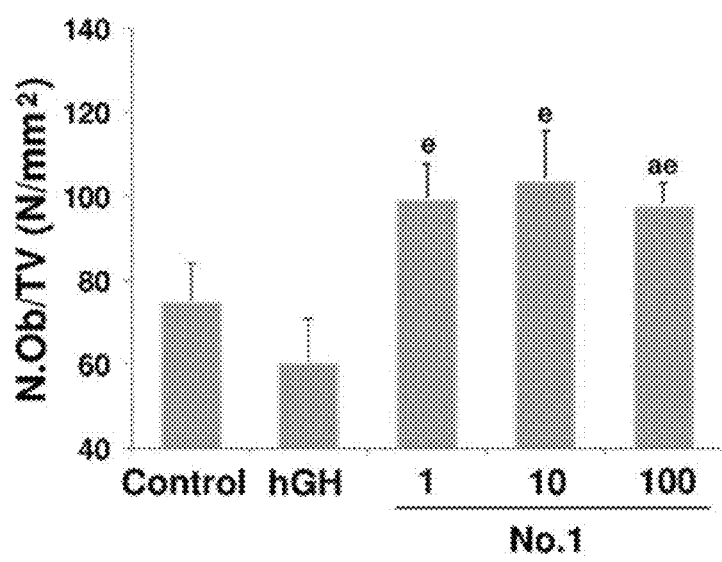
FIG. 28 is a chart showing the measurement results of the number of osteoblasts relative to the bone tissue volume in rats in a synthetic peptide administration group.
Figure 29:
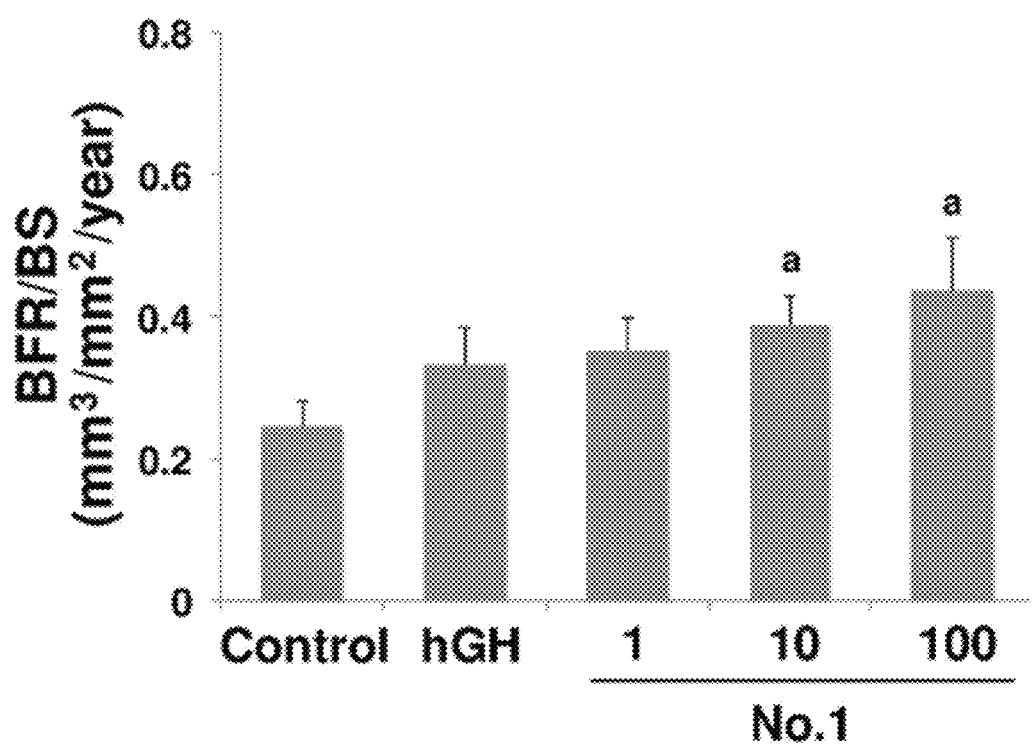
FIG. 29 is a chart showing the calculation results of the bone formation rate in a synthetic peptide administration group.

Study of Effect of Synthetic Peptides for Increasing Mineral Apposition Rate in Secondary Cancellous Bone One of the synthetic peptides (No. 1) or water for injection (control) was administered to Crlj:W1 male rats at four weeks old by oral gavage using a gastric tube once a day for seven days (n=10 in each group). The dose of the synthetic peptide was 1, 10 or 100 mg/kg·day. As a positive control, human growth hormone (hGH) (Norditropin, Standard Commodity Classification No. of Japan: 872412) was subcutaneously administered at 500 μg/kg·day once a day for seven days. As fluorescent labels for the site of bone formation, tetracycline (20 mg/kg) was subcutaneously administered on day 4 after the administration of the peptide or control, and then calcein (10 mg/kg) was subcutaneously administered on day 6 after the administration of the peptide or control. After the administration of the test sample on day 7, the rats were kept under fasting conditions. Twenty-four hours later, the rats were euthanized by bloodletting under anesthesia, and the tibiae were harvested. Non-decalcified specimens of the proximal tibiae were prepared and photographed under a fluorescent microscope (BX-53, OLYMPUS). The bone morphology was measured using a morphometry system (Histometry RT digitizer, System Supply Co., Ltd.) and an analysis software (CSS-840 cancellous bone morphometry version, System Supply Co., Ltd.). The mineral apposition rate (MAR), per day, in the secondary cancellous bone was determined by measuring the distance between the tetracycline label and the calcein label in the secondary cancellous bone, and dividing the distance by the administration interval between the fluorescent labels (two days). The results revealed a significant increase in the mineral apposition rate in the hGH administration group and the No. 1 administration group as compared with the control group. The No. 1 administration group also showed a significant increase in the mineral apposition rate at a dose of 10 mg/kg·day or more as compared with the hGH administration group (FIG. 26). The No. 1 administration group also showed a high percentage of the bone surface occupied by osteoblasts relative to the total bone surface (osteoblast surface/bone surface (Ob.S/BS)) (FIG. 27) and a high number of osteoblasts relative to the bone tissue volume (number of osteoblasts/tissue volume (N.Ob/TV)) (FIG. 28). The increase in the mineral apposition rate in the secondary cancellous bone in the No. 1 administration group would have resulted from the increase in the number of osteoblasts. The bone formation rate calculated as the annual fractional volume of bone formed relative to the bone surface (bone formation rate/bone surface (BFR/BS)) resulted in high rates in the No. 1 administration group (FIG. 29). The No. 1 administration group also showed a significant increase in the bone formation rate at a dose of 10 mg/kg-day or more as compared with the control group.

It is apparent from the above results that oral administration of the peptides of the present invention promotes mineral apposition of the secondary cancellous bone and increases the bone formation rate.

The present invention is not limited to each of the embodiments and Examples described above, and various modifications are possible within the scope of the claims.

Embodiments obtainable by appropriately combining the technical means disclosed in different embodiments of the present invention are also included in the technical scope of the present invention. The contents of the scientific literature and the patent literature cited herein are hereby incorporated by reference in their entirety.

The invention claimed is:

1. A method for promoting bone formation, the method comprising administering, to a mammal in need thereof, an effective amount of a peptide or a salt thereof having osteoblast growth-promoting activity, wherein said peptide consists of an amino acid sequence selected from the group consisting of:

(i) Val-Asn-Pro-Glu-Ser-Glu-Glu-Glu-Asp-Glu-Ser-Ser-Pro-Tyr-Glu, (SEQ ID NO: 1)

(ii) Val-Asn-Pro-Glu-Ser-Glu-Glu-Glu, (SEQ ID NO: 2)

-continued (iii) Val-Asn-Pro-Glu-Ser-Glu-Glu, (SEQ ID NO: 3)

(iv) Pro-Glu-Ser-Glu-Glu, (SEQ ID NO: 4)

(v) Asp-Glu-Ser-Ser-Pro-Tyr-Glu, (SEQ ID NO: 5)
and (vi) Glu-Asp-Glu-Ser-Ser-Pro-Tyr-Glu, (SEQ ID NO: 6)

wherein the peptide has at least one phosphorylated serine, and wherein the peptide promotes chondrocyte growth, induces chondrogenic cell differentiation, promotes hyaluronic acid production, promotes mesenchymal stem cell growth, induces mesenchymal stem cell differentiation, or increases the serum level of insulin-like growth factor (IGF-1) in the mammal.

2. The method of claim 1, wherein the peptide consists of the amino acid sequence of: (ii) Val-Asn-Pro-Glu-Ser-Glu-Glu-Glu (SEQ ID NO: 2).

3. The method of claim 1, wherein the peptide has the activity of inhibition of bone resorption.

4. The method of claim 1, wherein the peptide is administered orally.

5. The method of claim 1, wherein the peptide is included in a medicament, a food or drink, a supplement, a food additive or a cosmetic product.

* * * * *

UNITED STATES PATENT AND TRADEMARK OFFICE
CERTIFICATE OF CORRECTION

PATENT NO. : 10,538,564 B2
APPLICATION NO. : 15/121471
DATED : January 21, 2020
INVENTOR(S) : Chihiro Yamazaki et al.

It is certified that error appears in the above-identified patent and that said Letters Patent is hereby corrected as shown below:

In the Specification

In Column 4, Line 34, "[5]or" should read --[5] or--; and

In Column 4, Line 35, "lipovitellin-9" should read --lipovitellin-1--;

In Column 8, Line 7, "azacycloakane" should read --azacycloalkane--;

In Column 11, Line 26, "nethods" should read --methods--;

In Column 15, Line 12, "K;" should read --$K_2$--;

In Column 24, Line 27, "mg/kg-day." should read --mg/kg day.--;

In Column 24, Line 30, "µg/kg-day" should read --µg/kg day--;

In Column 26, Line 14, "mg/kg-day." should read --mg/kg day.--;

In Column 26, Line 60, "mg/kg-day." should read --mg/kg day--.

Signed and Sealed this
Second Day of June, 2020

Andrei Iancu
*Director of the United States Patent and Trademark Office*

```
                            SEQUENCE LISTING

<160> NUMBER OF SEQ ID NOS: 14

<210> SEQ ID NO 1
<211> LENGTH: 15
<212> TYPE: PRT
<213> ORGANISM: Artificial Sequence
<220> FEATURE:
<223> OTHER INFORMATION: Peptide

<400> SEQUENCE: 1

Val Asn Pro Glu Ser Glu Glu Asp Glu Ser Ser Pro Tyr Glu
1               5                   10                  15

<210> SEQ ID NO 2
<211> LENGTH: 8
<212> TYPE: PRT
<213> ORGANISM: Artificial Sequence
<220> FEATURE:
<223> OTHER INFORMATION: Peptide

<400> SEQUENCE: 2

Val Asn Pro Glu Ser Glu Glu Glu
1               5

<210> SEQ ID NO 3
<211> LENGTH: 7
<212> TYPE: PRT
<213> ORGANISM: Artificial Sequence
<220> FEATURE:
<223> OTHER INFORMATION: Peptide

<400> SEQUENCE: 3

Val Asn Pro Glu Ser Glu Glu
1               5

<210> SEQ ID NO 4
<211> LENGTH: 5
<212> TYPE: PRT
<213> ORGANISM: Artificial Sequence
<220> FEATURE:
<223> OTHER INFORMATION: Peptide

<400> SEQUENCE: 4

Pro Glu Ser Glu Glu
1               5

<210> SEQ ID NO 5
<211> LENGTH: 7
<212> TYPE: PRT
<213> ORGANISM: Artificial Sequence
<220> FEATURE:
<223> OTHER INFORMATION: Peptide

<400> SEQUENCE: 5

Asp Glu Ser Ser Pro Tyr Glu
1               5

<210> SEQ ID NO 6
<211> LENGTH: 8
<212> TYPE: PRT
<213> ORGANISM: Artificial Sequence
<220> FEATURE:
<223> OTHER INFORMATION: Peptide
```

<400> SEQUENCE: 6

```
Glu Asp Glu Ser Ser Pro Tyr Glu
1               5
```

<210> SEQ ID NO 7
<211> LENGTH: 1850
<212> TYPE: PRT
<213> ORGANISM: Gallus gallus

<400> SEQUENCE: 7

```
Met Arg Gly Ile Ile Leu Ala Leu Val Leu Thr Leu Val Gly Ser Gln
1               5                   10                  15

Lys Phe Asp Ile Asp Pro Gly Phe Asn Ser Arg Arg Ser Tyr Leu Tyr
            20                  25                  30

Asn Tyr Glu Gly Ser Met Leu Asn Gly Leu Gln Asp Arg Ser Leu Gly
        35                  40                  45

Lys Ala Gly Val Arg Leu Ser Ser Lys Leu Glu Ile Ser Gly Leu Pro
50                  55                  60

Glu Asn Ala Tyr Leu Leu Lys Val Arg Ser Pro Gln Val Glu Glu Tyr
65                  70                  75                  80

Asn Gly Val Trp Pro Arg Asp Pro Phe Thr Arg Ser Lys Ile Thr
                85                  90                  95

Gln Val Ile Ser Ser Cys Phe Thr Arg Leu Phe Lys Phe Glu Tyr Ser
            100                 105                 110

Ser Gly Arg Ile Gly Asn Ile Tyr Ala Pro Glu Asp Cys Pro Asp Leu
        115                 120                 125

Cys Val Asn Ile Val Arg Gly Ile Leu Asn Met Phe Gln Met Thr Ile
130                 135                 140

Lys Lys Ser Gln Asn Val Tyr Glu Leu Gln Glu Ala Gly Ile Gly Gly
145                 150                 155                 160

Ile Cys His Ala Arg Tyr Val Ile Gln Glu Asp Arg Lys Asn Ser Arg
                165                 170                 175

Ile Tyr Val Thr Arg Thr Val Asp Leu Asn Asn Cys Gln Glu Lys Val
            180                 185                 190

Gln Lys Ser Ile Gly Met Ala Tyr Ile Tyr Pro Cys Pro Val Asp Val
        195                 200                 205

Met Lys Glu Arg Leu Thr Lys Gly Thr Thr Ala Phe Ser Tyr Lys Leu
210                 215                 220

Lys Gln Ser Asp Ser Gly Thr Leu Ile Thr Asp Val Ser Ser Arg Gln
225                 230                 235                 240

Val Tyr Gln Ile Ser Pro Phe Asn Glu Pro Thr Gly Val Ala Val Met
                245                 250                 255

Glu Ala Arg Gln Gln Leu Thr Leu Val Arg Ser Glu Arg Gly
            260                 265                 270

Ser Ala Pro Asp Val Pro Met Gln Asn Tyr Gly Ser Leu Arg Tyr Arg
        275                 280                 285

Phe Pro Ala Val Leu Pro Gln Met Pro Leu Gln Leu Ile Lys Thr Lys
290                 295                 300

Asn Pro Glu Gln Arg Ile Val Glu Thr Leu Gln His Ile Val Leu Asn
305                 310                 315                 320

Asn Gln Gln Asp Phe His Asp Asp Val Ser Tyr Arg Phe Leu Glu Val
                325                 330                 335

Val Gln Leu Cys Arg Ile Ala Asn Ala Asp Asn Leu Glu Ser Ile Trp
            340                 345                 350
```

```
Arg Gln Val Ser Asp Lys Pro Arg Tyr Arg Trp Leu Leu Ser Ala
        355                 360                 365
Val Ser Ala Ser Gly Thr Thr Glu Thr Leu Lys Phe Leu Lys Asn Arg
370                 375                 380
Ile Arg Asn Asp Asp Leu Asn Tyr Ile Gln Thr Leu Leu Thr Val Ser
385                 390                 395                 400
Leu Thr Leu His Leu Leu Gln Ala Asp Glu His Thr Leu Pro Ile Ala
                405                 410                 415
Ala Asp Leu Met Thr Ser Ser Arg Ile Gln Lys Asn Pro Val Leu Gln
                420                 425                 430
Gln Val Ala Cys Leu Gly Tyr Ser Ser Val Val Asn Arg Tyr Cys Ser
                435                 440                 445
Gln Thr Ser Ala Cys Pro Lys Glu Ala Leu Gln Pro Ile His Asp Leu
                450                 455                 460
Ala Asp Glu Ala Ile Ser Arg Gly Arg Glu Asp Lys Met Lys Leu Ala
465                 470                 475                 480
Leu Lys Cys Ile Gly Asn Met Gly Glu Pro Ala Ser Leu Lys Arg Ile
                485                 490                 495
Leu Lys Phe Leu Pro Ile Ser Ser Ser Ala Ala Asp Ile Pro Val
                500                 505                 510
His Ile Gln Ile Asp Ala Ile Thr Ala Leu Lys Lys Ile Ala Trp Lys
                515                 520                 525
Asp Pro Lys Thr Val Gln Gly Tyr Leu Ile Gln Ile Leu Ala Asp Gln
                530                 535                 540
Ser Leu Pro Pro Glu Val Arg Met Met Ala Cys Ala Val Ile Phe Glu
545                 550                 555                 560
Thr Arg Pro Ala Leu Ala Leu Ile Thr Thr Ile Ala Asn Val Ala Met
                565                 570                 575
Lys Glu Ser Asn Met Gln Val Ala Ser Phe Val Tyr Ser His Met Lys
                580                 585                 590
Ser Leu Ser Lys Ser Arg Leu Pro Phe Met Tyr Asn Ile Ser Ser Ala
                595                 600                 605
Cys Asn Ile Ala Leu Lys Leu Leu Ser Pro Lys Leu Asp Ser Met Ser
                610                 615                 620
Tyr Arg Tyr Ser Lys Val Ile Arg Ala Asp Thr Tyr Phe Asp Asn Tyr
625                 630                 635                 640
Arg Val Gly Ala Thr Gly Glu Ile Phe Val Val Asn Ser Pro Arg Thr
                645                 650                 655
Met Phe Pro Ser Ala Ile Ile Ser Lys Leu Met Ala Asn Ser Ala Gly
                660                 665                 670
Ser Val Ala Asp Leu Val Glu Val Gly Ile Arg Val Glu Gly Leu Ala
                675                 680                 685
Asp Val Ile Met Lys Arg Asn Ile Pro Phe Ala Glu Tyr Pro Thr Tyr
                690                 695                 700
Lys Gln Ile Lys Glu Leu Gly Lys Ala Leu Gln Gly Trp Lys Glu Leu
705                 710                 715                 720
Pro Thr Glu Thr Pro Leu Val Ser Ala Tyr Leu Lys Ile Leu Gly Gln
                725                 730                 735
Glu Val Ala Phe Ile Asn Ile Asn Lys Glu Leu Leu Gln Gln Val Met
                740                 745                 750
Lys Thr Val Val Glu Pro Ala Asp Arg Asn Ala Ala Ile Lys Arg Ile
                755                 760                 765
```

-continued

```
Ala Asn Gln Ile Arg Asn Ser Ile Ala Gly Gln Trp Thr Gln Pro Val
770                 775                 780

Trp Met Gly Glu Leu Arg Tyr Val Val Pro Ser Cys Leu Gly Leu Pro
785                 790                 795                 800

Leu Glu Tyr Gly Ser Tyr Thr Thr Ala Leu Ala Arg Ala Ala Val Ser
                805                 810                 815

Val Glu Gly Lys Met Thr Pro Pro Leu Thr Gly Asp Phe Arg Leu Ser
            820                 825                 830

Gln Leu Leu Glu Ser Thr Met Gln Ile Arg Ser Asp Leu Lys Pro Ser
                835                 840                 845

Leu Tyr Val His Thr Val Ala Thr Met Gly Val Asn Thr Glu Tyr Phe
850                 855                 860

Gln His Ala Val Glu Ile Gln Gly Glu Val Gln Thr Arg Met Pro Met
865                 870                 875                 880

Lys Phe Asp Ala Lys Ile Asp Val Lys Leu Lys Asn Leu Lys Ile Glu
                885                 890                 895

Thr Asn Pro Cys Arg Glu Glu Thr Glu Ile Val Val Gly Arg His Lys
                900                 905                 910

Ala Phe Ala Val Ser Arg Asn Ile Gly Glu Leu Gly Val Glu Lys Arg
                915                 920                 925

Thr Ser Ile Leu Pro Glu Asp Ala Pro Leu Asp Val Thr Glu Glu Pro
930                 935                 940

Phe Gln Thr Ser Glu Arg Ala Ser Arg Glu His Phe Ala Met Gln Gly
945                 950                 955                 960

Pro Asp Ser Met Pro Arg Lys Gln Ser His Ser Arg Glu Asp Leu
                965                 970                 975

Arg Arg Ser Thr Gly Lys Arg Ala His Lys Arg Asp Ile Cys Leu Lys
                980                 985                 990

Met His His Ile Gly Cys Gln Leu Cys Phe Ser Arg Arg Ser Arg Asp
            995                 1000                1005

Ala Ser Phe Ile Gln Asn Thr Tyr Leu His Lys Leu Ile Gly Glu
        1010                1015                1020

His Glu Ala Lys Ile Val Leu Met Pro Val His Thr Asp Ala Asp
        1025                1030                1035

Ile Asp Lys Ile Gln Leu Glu Ile Gln Ala Gly Ser Arg Ala Ala
        1040                1045                1050

Ala Arg Ile Ile Thr Glu Val Asn Pro Glu Ser Glu Glu Glu Asp
        1055                1060                1065

Glu Ser Ser Pro Tyr Glu Asp Ile Gln Ala Lys Leu Lys Arg Ile
        1070                1075                1080

Leu Gly Ile Asp Ser Met Phe Lys Val Ala Asn Lys Thr Arg His
        1085                1090                1095

Pro Lys Asn Arg Pro Ser Lys Lys Gly Asn Thr Val Leu Ala Glu
        1100                1105                1110

Phe Gly Thr Glu Pro Asp Ala Lys Thr Ser Ser Ser Ser Ser Ser
        1115                1120                1125

Ala Ser Ser Thr Ala Thr Ser Ser Ser Ser Ser Ala Ser Ser
        1130                1135                1140

Pro Asn Arg Lys Lys Pro Met Asp Glu Glu Glu Asn Asp Gln Val
        1145                1150                1155

Lys Gln Ala Arg Asn Lys Asp Ala Ser Ser Ser Ser Arg Ser Ser
        1160                1165                1170

Lys Ser Ser Asn Ser Ser Lys Arg Ser Ser Ser Lys Ser Ser Asn
```

```
              1175                1180                1185

Ser  Ser  Lys  Arg  Ser  Ser  Ser  Ser  Ser  Ser  Ser  Ser  Ser
     1190                1195                1200

Ser  Arg  Ser  Ser  Ser  Ser  Ser  Ser  Ser  Ser  Asn  Ser  Lys
     1205                1210                1215

Ser  Ser  Ser  Ser  Ser  Ser  Lys  Ser  Ser  Ser  Ser  Ser  Arg  Ser
     1220                1225                1230

Arg  Ser  Ser  Ser  Lys  Ser  Ser  Ser  Ser  Ser  Ser  Ser  Ser  Ser
     1235                1240                1245

Ser  Ser  Ser  Ser  Lys  Ser  Ser  Ser  Ser  Arg  Ser  Ser  Ser  Ser
     1250                1255                1260

Ser  Lys  Ser  Ser  Ser  His  His  Ser  His  Ser  His  His  Ser  Gly  His
     1265                1270                1275

Leu  Asn  Gly  Ser  Ser  Ser  Ser  Ser  Ser  Ser  Ser  Arg  Ser  Val  Ser
     1280                1285                1290

His  His  Ser  His  Glu  His  His  Ser  Gly  His  Leu  Glu  Asp  Asp  Ser
     1295                1300                1305

Ser  Ser  Ser  Ser  Ser  Ser  Ser  Val  Leu  Ser  Lys  Ile  Trp  Gly  Arg
     1310                1315                1320

His  Glu  Ile  Tyr  Gln  Tyr  Arg  Phe  Arg  Ser  Ala  His  Arg  Gln  Glu
     1325                1330                1335

Phe  Pro  Lys  Arg  Lys  Leu  Pro  Gly  Asp  Arg  Ala  Thr  Ser  Arg  Tyr
     1340                1345                1350

Ser  Ser  Thr  Arg  Ser  Ser  His  Asp  Thr  Ser  Arg  Ala  Ala  Ser  Trp
     1355                1360                1365

Pro  Lys  Phe  Leu  Gly  Asp  Ile  Lys  Thr  Pro  Val  Leu  Ala  Ala  Phe
     1370                1375                1380

Leu  His  Gly  Ile  Ser  Asn  Asn  Lys  Lys  Thr  Gly  Gly  Leu  Gln  Leu
     1385                1390                1395

Val  Val  Tyr  Ala  Asp  Thr  Asp  Ser  Val  Arg  Pro  Arg  Val  Gln  Val
     1400                1405                1410

Phe  Val  Thr  Asn  Leu  Thr  Asp  Ser  Ser  Lys  Trp  Lys  Leu  Cys  Ala
     1415                1420                1425

Asp  Ala  Ser  Val  Arg  Asn  Ala  His  Lys  Ala  Val  Ala  Tyr  Val  Lys
     1430                1435                1440

Trp  Gly  Trp  Asp  Cys  Arg  Asp  Tyr  Lys  Val  Ser  Thr  Glu  Leu  Val
     1445                1450                1455

Thr  Gly  Arg  Phe  Ala  Gly  His  Pro  Ala  Ala  Gln  Val  Lys  Leu  Glu
     1460                1465                1470

Trp  Pro  Lys  Val  Pro  Ser  Asn  Val  Arg  Ser  Val  Val  Glu  Trp  Phe
     1475                1480                1485

Tyr  Glu  Phe  Val  Pro  Gly  Ala  Ala  Phe  Met  Leu  Gly  Phe  Ser  Glu
     1490                1495                1500

Arg  Met  Asp  Lys  Asn  Pro  Ser  Arg  Gln  Ala  Arg  Met  Val  Val  Ala
     1505                1510                1515

Leu  Thr  Ser  Pro  Arg  Thr  Cys  Asp  Val  Val  Lys  Leu  Pro  Asp
     1520                1525                1530

Ile  Ile  Leu  Tyr  Gln  Lys  Ala  Val  Arg  Leu  Pro  Leu  Ser  Leu  Pro
     1535                1540                1545

Val  Gly  Pro  Arg  Ile  Pro  Ala  Ser  Glu  Leu  Gln  Pro  Pro  Ile  Trp
     1550                1555                1560

Asn  Val  Phe  Ala  Glu  Ala  Pro  Ser  Ala  Val  Leu  Glu  Asn  Leu  Lys
     1565                1570                1575
```

```
Ala Arg Cys Ser Val Ser Tyr Asn Lys Ile Lys Thr Phe Asn Glu
        1580                1585                1590

Val Lys Phe Asn Tyr Ser Met Pro Ala Asn Cys Tyr His Ile Leu
        1595                1600                1605

Val Gln Asp Cys Ser Ser Glu Leu Lys Phe Leu Val Met Met Lys
        1610                1615                1620

Ser Ala Gly Glu Ala Thr Asn Leu Lys Ala Ile Asn Ile Lys Ile
        1625                1630                1635

Gly Ser His Glu Ile Asp Met His Pro Val Asn Gly Gln Val Lys
        1640                1645                1650

Leu Leu Val Asp Gly Ala Glu Ser Pro Thr Ala Asn Ile Ser Leu
        1655                1660                1665

Ile Ser Ala Gly Ala Ser Leu Trp Ile His Asn Glu Asn Gln Gly
        1670                1675                1680

Phe Ala Leu Ala Ala Pro Gly His Gly Ile Asp Lys Leu Tyr Phe
        1685                1690                1695

Asp Gly Lys Thr Ile Thr Ile Gln Val Pro Leu Trp Met Ala Gly
        1700                1705                1710

Lys Thr Cys Gly Ile Cys Gly Lys Tyr Asp Ala Glu Cys Glu Gln
        1715                1720                1725

Glu Tyr Arg Met Pro Asn Gly Tyr Leu Ala Lys Asn Ala Val Ser
        1730                1735                1740

Phe Gly His Ser Trp Ile Leu Glu Glu Ala Pro Cys Arg Gly Ala
        1745                1750                1755

Cys Lys Leu His Arg Ser Phe Val Lys Leu Glu Lys Thr Val Gln
        1760                1765                1770

Leu Ala Gly Val Asp Ser Lys Cys Tyr Ser Thr Glu Pro Val Leu
        1775                1780                1785

Arg Cys Ala Lys Gly Cys Ser Ala Thr Lys Thr Thr Pro Val Thr
        1790                1795                1800

Val Gly Phe His Cys Leu Pro Ala Asp Ser Ala Asn Ser Leu Thr
        1805                1810                1815

Asp Lys Gln Met Lys Tyr Asp Gln Lys Ser Glu Asp Met Gln Asp
        1820                1825                1830

Thr Val Asp Ala His Thr Thr Cys Ser Cys Glu Asn Glu Glu Cys
        1835                1840                1845

Ser Thr
    1850

<210> SEQ ID NO 8
<211> LENGTH: 1096
<212> TYPE: PRT
<213> ORGANISM: Gallus gallus

<400> SEQUENCE: 8

Gln Lys Phe Asp Ile Asp Pro Gly Phe Asn Ser Arg Arg Ser Tyr Leu
 1               5                   10                  15

Tyr Asn Tyr Glu Gly Ser Met Leu Asn Gly Leu Gln Asp Arg Ser Leu
            20                  25                  30

Gly Lys Ala Gly Val Arg Leu Ser Lys Leu Glu Ile Ser Gly Leu
        35                  40                  45

Pro Glu Asn Ala Tyr Leu Leu Lys Val Arg Ser Pro Gln Val Glu Glu
    50                  55                  60

Tyr Asn Gly Val Trp Pro Arg Asp Pro Phe Thr Arg Ser Ser Lys Ile
```

-continued

```
             65                  70                  75                  80
Thr Gln Val Ile Ser Ser Cys Phe Thr Arg Leu Phe Lys Phe Glu Tyr
                         85                  90                  95
Ser Ser Gly Arg Ile Gly Asn Ile Tyr Ala Pro Glu Asp Cys Pro Asp
                 100                 105                 110
Leu Cys Val Asn Ile Val Arg Gly Ile Leu Asn Met Phe Gln Met Thr
             115                 120                 125
Ile Lys Lys Ser Gln Asn Val Tyr Glu Leu Gln Glu Ala Gly Ile Gly
         130                 135                 140
Gly Ile Cys His Ala Arg Tyr Val Ile Gln Glu Asp Arg Lys Asn Ser
145                 150                 155                 160
Arg Ile Tyr Val Thr Arg Thr Val Asp Leu Asn Asn Cys Gln Glu Lys
                     165                 170                 175
Val Gln Lys Ser Ile Gly Met Ala Tyr Ile Tyr Pro Cys Pro Val Asp
                 180                 185                 190
Val Met Lys Glu Arg Leu Thr Lys Gly Thr Thr Ala Phe Ser Tyr Lys
             195                 200                 205
Leu Lys Gln Ser Asp Ser Gly Thr Leu Ile Thr Asp Val Ser Ser Arg
         210                 215                 220
Gln Val Tyr Gln Ile Ser Pro Phe Asn Glu Pro Thr Gly Val Ala Val
225                 230                 235                 240
Met Glu Ala Arg Gln Gln Leu Thr Leu Val Glu Val Arg Ser Glu Arg
                     245                 250                 255
Gly Ser Ala Pro Asp Val Pro Met Gln Asn Tyr Gly Ser Leu Arg Tyr
                 260                 265                 270
Arg Phe Pro Ala Val Leu Pro Gln Met Pro Leu Gln Leu Ile Lys Thr
             275                 280                 285
Lys Asn Pro Glu Gln Arg Ile Val Glu Thr Leu Gln His Ile Val Leu
         290                 295                 300
Asn Asn Gln Gln Asp Phe His Asp Asp Val Ser Tyr Arg Phe Leu Glu
305                 310                 315                 320
Val Val Gln Leu Cys Arg Ile Ala Asn Ala Asp Asn Leu Glu Ser Ile
                     325                 330                 335
Trp Arg Gln Val Ser Asp Lys Pro Arg Tyr Arg Arg Trp Leu Leu Ser
                 340                 345                 350
Ala Val Ser Ala Ser Gly Thr Thr Glu Thr Leu Lys Phe Leu Lys Asn
             355                 360                 365
Arg Ile Arg Asn Asp Asp Leu Asn Tyr Ile Gln Thr Leu Leu Thr Val
         370                 375                 380
Ser Leu Thr Leu His Leu Leu Gln Ala Asp Glu His Thr Leu Pro Ile
385                 390                 395                 400
Ala Ala Asp Leu Met Thr Ser Ser Arg Ile Gln Lys Asn Pro Val Leu
                     405                 410                 415
Gln Gln Val Ala Cys Leu Gly Tyr Ser Ser Val Val Asn Arg Tyr Cys
                 420                 425                 430
Ser Gln Thr Ser Ala Cys Pro Lys Glu Ala Leu Gln Pro Ile His Asp
             435                 440                 445
Leu Ala Asp Glu Ala Ile Ser Arg Gly Arg Glu Asp Lys Met Lys Leu
         450                 455                 460
Ala Leu Lys Cys Ile Gly Asn Met Gly Glu Pro Ala Ser Leu Lys Arg
465                 470                 475                 480
Ile Leu Lys Phe Leu Pro Ile Ser Ser Ser Ala Ala Asp Ile Pro
                     485                 490                 495
```

-continued

```
Val His Ile Gln Ile Asp Ala Ile Thr Ala Leu Lys Lys Ile Ala Trp
            500                 505                 510
Lys Asp Pro Lys Thr Val Gln Gly Tyr Leu Ile Gln Ile Leu Ala Asp
        515                 520                 525
Gln Ser Leu Pro Pro Glu Val Arg Met Met Ala Cys Ala Val Ile Phe
    530                 535                 540
Glu Thr Arg Pro Ala Leu Ala Leu Ile Thr Thr Ile Ala Asn Val Ala
545                 550                 555                 560
Met Lys Glu Ser Asn Met Gln Val Ala Ser Phe Val Tyr Ser His Met
                565                 570                 575
Lys Ser Leu Ser Lys Ser Arg Leu Pro Phe Met Tyr Asn Ile Ser Ser
            580                 585                 590
Ala Cys Asn Ile Ala Leu Lys Leu Leu Ser Pro Lys Leu Asp Ser Met
        595                 600                 605
Ser Tyr Arg Tyr Ser Lys Val Ile Arg Ala Asp Thr Tyr Phe Asp Asn
    610                 615                 620
Tyr Arg Val Gly Ala Thr Gly Glu Ile Phe Val Asn Ser Pro Arg
625                 630                 635                 640
Thr Met Phe Pro Ser Ala Ile Ile Ser Lys Leu Met Ala Asn Ser Ala
                645                 650                 655
Gly Ser Val Ala Asp Leu Val Glu Val Gly Ile Arg Val Glu Gly Leu
            660                 665                 670
Ala Asp Val Ile Met Lys Arg Asn Ile Pro Phe Ala Glu Tyr Pro Thr
        675                 680                 685
Tyr Lys Gln Ile Lys Glu Leu Gly Lys Ala Leu Gln Gly Trp Lys Glu
    690                 695                 700
Leu Pro Thr Glu Thr Pro Leu Val Ser Ala Tyr Leu Lys Ile Leu Gly
705                 710                 715                 720
Gln Glu Val Ala Phe Ile Asn Ile Asn Lys Glu Leu Leu Gln Gln Val
                725                 730                 735
Met Lys Thr Val Val Glu Pro Ala Asp Arg Asn Ala Ala Ile Lys Arg
            740                 745                 750
Ile Ala Asn Gln Ile Arg Asn Ser Ile Ala Gly Gln Trp Thr Gln Pro
        755                 760                 765
Val Trp Met Gly Glu Leu Arg Tyr Val Val Pro Ser Cys Leu Gly Leu
    770                 775                 780
Pro Leu Glu Tyr Gly Ser Tyr Thr Thr Ala Leu Ala Arg Ala Ala Val
785                 790                 795                 800
Ser Val Glu Gly Lys Met Thr Pro Pro Leu Thr Gly Asp Phe Arg Leu
                805                 810                 815
Ser Gln Leu Leu Glu Ser Thr Met Gln Ile Arg Ser Asp Leu Lys Pro
            820                 825                 830
Ser Leu Tyr Val His Thr Val Ala Thr Met Gly Val Asn Thr Glu Tyr
        835                 840                 845
Phe Gln His Ala Val Glu Ile Gln Gly Glu Val Gln Thr Arg Met Pro
    850                 855                 860
Met Lys Phe Asp Ala Lys Ile Asp Val Lys Leu Lys Asn Leu Lys Ile
865                 870                 875                 880
Glu Thr Asn Pro Cys Arg Glu Thr Glu Ile Val Val Gly Arg His
                885                 890                 895
Lys Ala Phe Ala Val Ser Arg Asn Ile Gly Glu Leu Gly Val Glu Lys
            900                 905                 910
```

-continued

Arg Thr Ser Ile Leu Pro Glu Asp Ala Pro Leu Asp Val Thr Glu Glu
        915                 920                 925

Pro Phe Gln Thr Ser Glu Arg Ala Ser Arg Glu His Phe Ala Met Gln
    930                 935                 940

Gly Pro Asp Ser Met Pro Arg Lys Gln Ser His Ser Arg Glu Asp
945                 950                 955                 960

Leu Arg Arg Ser Thr Gly Lys Arg Ala His Lys Arg Asp Ile Cys Leu
                965                 970                 975

Lys Met His His Ile Gly Cys Gln Leu Cys Phe Ser Arg Arg Ser Arg
            980                 985                 990

Asp Ala Ser Phe Ile Gln Asn Thr Tyr Leu His Lys Leu Ile Gly Glu
        995                 1000                1005

His Glu Ala Lys Ile Val Leu Met Pro Val His Thr Asp Ala Asp
    1010                1015                1020

Ile Asp Lys Ile Gln Leu Glu Ile Gln Ala Gly Ser Arg Ala Ala
    1025                1030                1035

Ala Arg Ile Ile Thr Glu Val Asn Pro Glu Ser Glu Glu Glu Asp
    1040                1045                1050

Glu Ser Ser Pro Tyr Glu Asp Ile Gln Ala Lys Leu Lys Arg Ile
    1055                1060                1065

Leu Gly Ile Asp Ser Met Phe Lys Val Ala Asn Lys Thr Arg His
    1070                1075                1080

Pro Lys Asn Arg Pro Ser Lys Lys Gly Asn Thr Val Leu
    1085                1090                1095

<210> SEQ ID NO 9
<211> LENGTH: 8
<212> TYPE: PRT
<213> ORGANISM: Artificial Sequence
<220> FEATURE:
<223> OTHER INFORMATION: Phosphopeptide
<220> FEATURE:
<221> NAME/KEY: PHOSPHORYLATION
<222> LOCATION: (5)..(5)
<223> OTHER INFORMATION:

<400> SEQUENCE: 9

Val Asn Pro Glu Ser Glu Glu Glu
1               5

<210> SEQ ID NO 10
<211> LENGTH: 7
<212> TYPE: PRT
<213> ORGANISM: Artificial Sequence
<220> FEATURE:
<223> OTHER INFORMATION: Phosphopeptide
<220> FEATURE:
<221> NAME/KEY: PHOSPHORYLATION
<222> LOCATION: (5)..(5)
<223> OTHER INFORMATION:

<400> SEQUENCE: 10

Val Asn Pro Glu Ser Glu Glu
1               5

<210> SEQ ID NO 11
<211> LENGTH: 5
<212> TYPE: PRT

```
<213> ORGANISM: Artificial Sequence
<220> FEATURE:
<223> OTHER INFORMATION: Phosphopeptide
<220> FEATURE:
<221> NAME/KEY: PHOSPHORYLATION
<222> LOCATION: (3)..(3)
<223> OTHER INFORMATION:

<400> SEQUENCE: 11

Pro Glu Ser Glu Glu
1               5

<210> SEQ ID NO 12
<211> LENGTH: 7
<212> TYPE: PRT
<213> ORGANISM: Artificial Sequence
<220> FEATURE:
<223> OTHER INFORMATION: Phosphopeptide
<220> FEATURE:
<221> NAME/KEY: PHOSPHORYLATION
<222> LOCATION: (3)..(3)
<223> OTHER INFORMATION:

<400> SEQUENCE: 12

Asp Glu Ser Ser Pro Tyr Glu
1               5

<210> SEQ ID NO 13
<211> LENGTH: 8
<212> TYPE: PRT
<213> ORGANISM: Artificial Sequence
<220> FEATURE:
<223> OTHER INFORMATION: Phosphopeptide
<220> FEATURE:
<221> NAME/KEY: PHOSPHORYLATION
<222> LOCATION: (4)..(4)
<223> OTHER INFORMATION:

<400> SEQUENCE: 13

Glu Asp Glu Ser Ser Pro Tyr Glu
1               5

<210> SEQ ID NO 14
<211> LENGTH: 15
<212> TYPE: PRT
<213> ORGANISM: Artificial Sequence
<220> FEATURE:
<223> OTHER INFORMATION: Phosphopeptide
<220> FEATURE:
<221> NAME/KEY: PHOSPHORYLATION
<222> LOCATION: (5)..(5)
<223> OTHER INFORMATION:
<220> FEATURE:
<221> NAME/KEY: PHOSPHORYLATION
<222> LOCATION: (11)..(11)
<223> OTHER INFORMATION:

<400> SEQUENCE: 14

Val Asn Pro Glu Ser Glu Glu Glu Asp Glu Ser Ser Pro Tyr Glu
1               5                   10                  15
```